US005846747A

United States Patent [19]

Thorens et al.

[11] Patent Number: 5,846,747

[45] Date of Patent: Dec. 8, 1998

[54] METHOD FOR DETECTING GLUCAGON-LIKE PEPTIDE-1 ANTAGONISTS AND AGONISTS

[75] Inventors: Bernard Thorens, Epalinges, Switzerland; Liselotte Bjerre Knudsen, Valby, Denmark

[73] Assignee: Novo Nordisk A/S, Bagsvaerd, Denmark

[21] Appl. No.: 869,477

[22] Filed: Jun. 5, 1997

Related U.S. Application Data

[63] Continuation-in-part of Ser. No. 142,439, Nov. 24, 1993, Pat. No. 5,670,360.

[30] Foreign Application Priority Data

Mar. 25, 1993 [DK] Denmark .................................. 398/92

[51] Int. Cl.$^{6}$ ............................ C12N 15/12; C07K 14/72

[52] U.S. Cl. ............................ 435/7.21; 435/7.1; 435/29

[58] Field of Search .................................... 435/7.21, 7.1, 435/29

[56] References Cited

U.S. PATENT DOCUMENTS 5,670,360 9/1997 Thorens .................................. 435/325

OTHER PUBLICATIONS

Saxena et al., Biochemistry, vol. 25, pp. 7943–7950 (1986).

Jüppner et al., Science, vol. 254, pp. 1024–1026 (1991).

Lin et al., Science, vol. 254, pp. 1022–1024 (1991).

Göke et al., FEBS Letters, vol. 300, No. 3, pp. 232–236 (1992).

*Primary Examiner*—David L. Fitzgerald

*Attorney, Agent, or Firm*—Steve T. Zelson, Esq.; Valeta Gregg, Esq.

[57] ABSTRACT

The present invention relates to a recombinant glucagon-like peptide-1 (GLP-1) receptor, to a DNA construct which comprises a DNA sequence encoding a GLP-1 receptor, to methods of screening for antagonists of GLP-1 activity, and to the use of the GLP-1 receptor for screening for antagonists of GLP-1 activity.

12 Claims, 8 Drawing Sheets

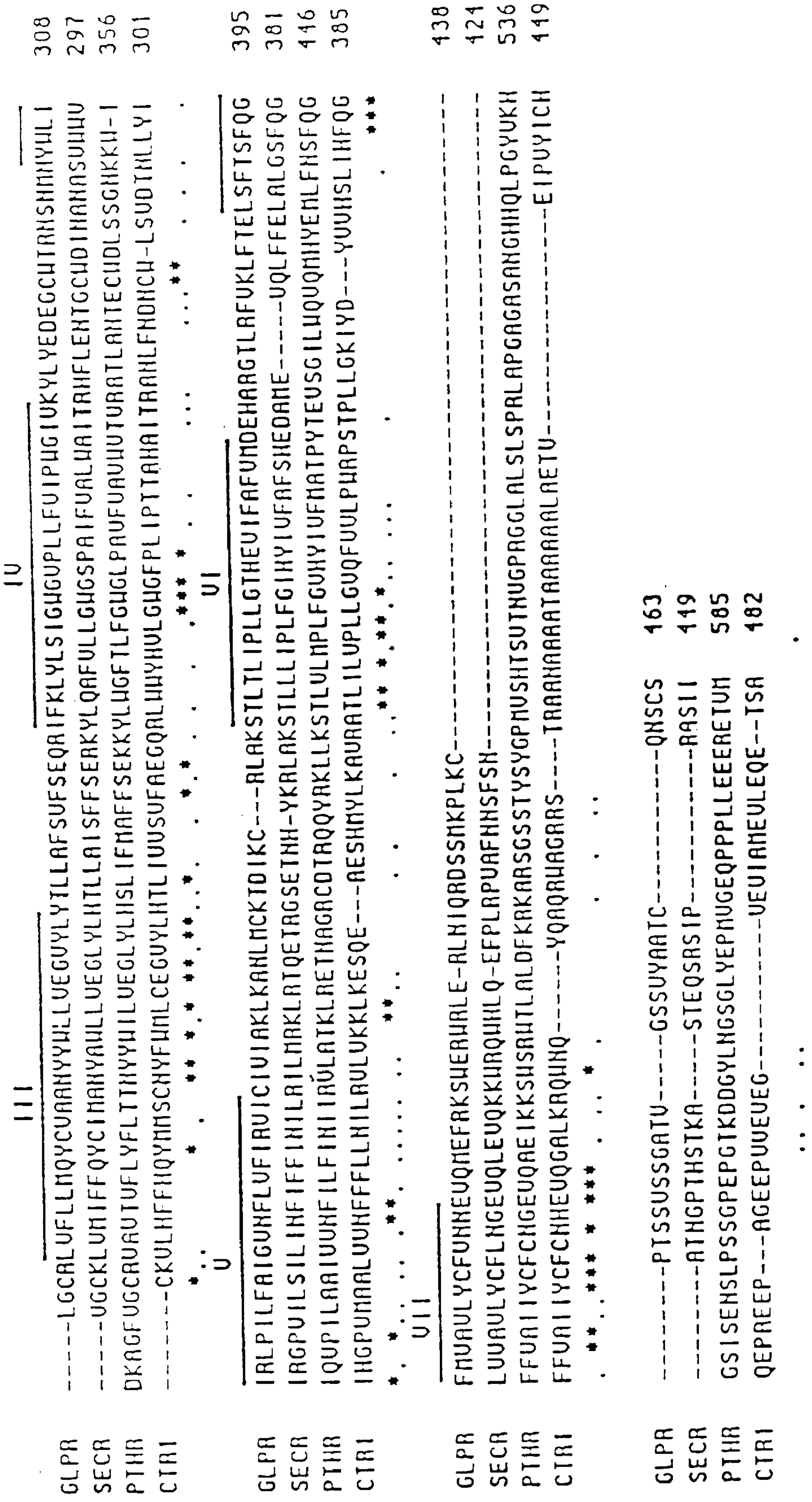

FIG. 1B

```
                    III                                                                                     IV
GLPR    ------LGCRLVFLILNQYCWANYYWLVEGVYLYILLAFSVFSEQAIFKLYLSIGWGVPLLFVIPWGIVKYLVEDEGCWTRNSWHYWLI         308
SECR    ------VGCKLVHIFFQYCIHAVYAVLLVEGLYLHTLLAISFFSERKYLQAFVLLGWGSPAIFVALHAITRHFLEHTGCWDIHAHASWHHW         297
PTHR    DKAGFVGCRVAVTVFLYFLTTHYYHILVEGLYLIISLIFHAFFSEKKYLWGFTLFGVGLPAVFVAVVVTVRATLAHTECIIDLSSGHKKW-I         356
CTR1    ------CKVLHFFHQYHHSCHYFWHLCEGVYLHTLIVVSVFAEGQRLHHYHVLGWGFPLIPTTAHAITRAHLFHDHCW-LSVDTHLLYI         301
                .  **  .   .  *   ** **    .      ** ** ..* :.  . .. .   :  .
                                           V                              VI
GLPR    IRLPILFAIGVHFLVFIRVICIVIAKLKAHLHCKTDIKC----ALAKSTLTLIPLLGTHEVIFAFVHDEHARGTLRFVKLFTELSFTSFQG         395
SECR    IRGPVILSILIHFIFFIHILAIHARKLRTQETARGSETHH-YKRLAKSTLLLIPLFGIHYIVFAFSHEDAHE------VQLFFELALGSFQG         381
PTHR    IQVPILAAIVVHFILFIHIIRVLATKLRETHAGACDTRQQYRKLLKSTLVLHPLFGVHYIVFHATPYTEVSGILHQVQMHYEMLFHSFQG         446
CTR1    IHGPVHAALVVHFFFLLHILAVLVKKLKESQE----AESHHYLKAVRATLILVPLLGVQFVVLPWRPSTPLLGKIYD----YVVHSLIHFQG         385
            *. * *.  :  .* *   .   ** *.    :.                        *:.*
                VII
GLPR    FHVAVLYCFVHHEVQHEFRKSWERWALE-ALHIQRDSSHKPLKC--------------------------------------------         438
SECR    LVVAVLYCFLHGEVQLEVQKKWRQWHLQ-EFPLRPVAFHHSFSH--------------------------------------------         421
PTHR    FFVAIIYCFCHGEVQAEIKKSWSRWTLALDFKRKARSGSSTYSYGPHVSHTSVTHVGPAGGIALSLSPRLAPGASAHGHHQLPGYVKH         536
CTR1    FFVAIIYCFCHHEVQGALKRQWHQ--------YQAQWAGRAS-----------TRAAHAAATAAAALRETV-----------EIPVYICH         449
         * .*** *  .                                          .
GLPR    --------PTSSVSSGATV------GSSVYAATC----------QHSCS         463
SECR    --------ATHGPTHSTKA-------STEQSRSIP----------RASII         449
PTHR    GSISEHSLPSSGPEPGTKDDGYLHGSGLYEPHVGEQPPPLLEERETVH         585
CTR1    QEPREEP---AGEEPVVEVEG-----------VEVIAHEVLEQE--TSA         482
```

```
RAT - MAVTPSLLRLALLLLGAVGRAGPRPQGATVSLSETVQKWREYRHQCQRFL - 50

RAT - TEAPLLATGLFCNRTFDDYACWPDGPPGSFVNVSCPWYLPWASSVLQGHV -100

RAT - YRFCTAEGIWLHKDNSSLPWRDLSECEESKQGERNSPEEQLLSLYIIYTV -150

RAT - GYALSFSALVIASAILVSFRHLHCTRNYIHLNLFASFILRALSVFIKDAA -200
                         ::: :::::::::::::::::::::::::::
HUM -                    RHLYCTRNYIHLNLFASFILRALSVFIKDAA - 31

RAT - LKWMYSTAAQQHQWDGLLSYQDSLGCRLVFLLMQYCVAANYYWLLVEGVY -250
      :::::::::::::::::::::::: :::::::::::::::::::::::::
HUM - LKWMYSTAAQQHQWDGLLSYQDSLSCRLVFLLMQYCVAANYYWLLVEGVY - 81

RAT - LYTLLAFSVFSEQRIFKLYLSIGWGVPLLFVIPWGIVKYLYEDEGCWTRN -300
      ::::::::::::: :: :: ::::::::::: :::::: :::::::::::
HUM - LYTLLAFSVFSEQWIFRLYVSIGWGVPLLFVVPWGIVKILYEDEGCWTRN -131

RAT - SNMNYWLIIRLPILFAIGVNFLVFIRVICIVIAKLKANLMCKTDIKCRLA -350
      :::::::::::::::::::::: : ::::::  :::::::::::::::::
HUM - SNMNYWLIIRLPILFAIGVNFLIFVRVICIVVSKLKANLMCKTDIKCRLA -181

RAT - KSTLTLIPLLGTHEVIFAFVMDEHARGTLRFVKLFTELSFTSFQGFMVAV -400
      ::::::::::::::::::::::::::::::: ::::::::::::: :::
HUM - KSTLTLIPLLGTHEVIFAFVMDEHARGTLRFIKLFTELSFTSFQGLMVAI -231

RAT - LYCFVNNEVQMEFRKSWERWRLERLNIQRDSSMKPLKCPTSSVSSGATVG -450
      :::::::::: :::::::::::: : :::::::::::::::: ::::: :
HUM - LYCFVNNEVQLEFRKSWERWRLEHLHIQRDSSMKPLKCPTSSLSSGATAG -281

RAT - SSVYAATCQNSCS -463
      :: : :::: :::
HUM - SSMYTATCQASCS -294
```

FIG. 7

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 3066 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( v i ) ORIGINAL SOURCE:
( A ) ORGANISM: Rat ( i x ) FEATURE:
( A ) NAME/KEY: CDS
( B ) LOCATION: 17..1408

( x i ) SEQUENCE DESCRIPTION: SEQ ID NO:1:

```
TCCTGAGCGC CCCGCC ATG GCC GTC ACC CCC AGC CTG CTG CGC CTG GCG         49
                  Met Ala Val Thr Pro Ser Leu Leu Arg Leu Ala
                   1               5                  10

CTC CTG CTG CTC GGG GCG GTG GGC AGG GCC GGC CCC CGC CCC CAG GGT       97
Leu Leu Leu Leu Gly Ala Val Gly Arg Ala Gly Pro Arg Pro Gln Gly
             15                  20                  25

GCC ACG GTG TCC CTC TCA GAG ACA GTG CAG AAA TGG AGA GAG TAT CGG      145
Ala Thr Val Ser Leu Ser Glu Thr Val Gln Lys Trp Arg Glu Tyr Arg
         30                  35                  40

CAC CAG TGC CAA CGT TTC CTC ACG GAA GCG CCA CTC CTG GCC ACA GGT      193
His Gln Cys Gln Arg Phe Leu Thr Glu Ala Pro Leu Leu Ala Thr Gly
     45                  50                  55

CTC TTC TGC AAC CGA ACC TTT GAT GAC TAC GCC TGC TGG CCA GAT GGG      241
Leu Phe Cys Asn Arg Thr Phe Asp Asp Tyr Ala Cys Trp Pro Asp Gly
 60                  65                  70                  75

CCC CCA GGT TCC TTT GTG AAT GTC AGT TGC CCC TGG TAC CTG CCG TGG      289
Pro Pro Gly Ser Phe Val Asn Val Ser Cys Pro Trp Tyr Leu Pro Trp
                 80                  85                  90

GCC AGT AGT GTG CTC CAA GGG CAT GTG TAC CGG TTC TGC ACG GCC GAG      337
Ala Ser Ser Val Leu Gln Gly His Val Tyr Arg Phe Cys Thr Ala Glu
             95                 100                 105
```

-continued

GGT ATC TGG CTG CAT AAG GAC AAC TCC AGC CTG CCC TGG AGG GAC CTG 385
Gly Ile Trp Leu His Lys Asp Asn Ser Ser Leu Pro Trp Arg Asp Leu
110 115 120

TCG GAG TGC GAA GAG TCC AAG CAA GGA GAG AGA AAC TCC CCT GAG GAA 433
Ser Glu Cys Glu Glu Ser Lys Gln Gly Glu Arg Asn Ser Pro Glu Glu
125 130 135

CAG CTC CTG TCG CTG TAC ATT ATC TAC ACG GTG GGG TAC GCA CTT TCT 481
Gln Leu Leu Ser Leu Tyr Ile Ile Tyr Thr Val Gly Tyr Ala Leu Ser
140 145 150 155

TTC TCT GCC TTG GTC ATC GCT TCA GCC ATC CTT GTC AGC TTC AGA CAC 529
Phe Ser Ala Leu Val Ile Ala Ser Ala Ile Leu Val Ser Phe Arg His
160 165 170

TTG CAC TGC ACC AGG AAC TAC ATC CAC CTG AAC CTG TTT GCG TCC TTC 577
Leu His Cys Thr Arg Asn Tyr Ile His Leu Asn Leu Phe Ala Ser Phe
175 180 185

ATC CTC CGA GCA CTG TCC GTC TTC ATC AAA GAC GCT GCC CTC AAG TGG 625
Ile Leu Arg Ala Leu Ser Val Phe Ile Lys Asp Ala Ala Leu Lys Trp
190 195 200

ATG TAT AGC ACG GCT GCG CAA CAG CAC CAG TGG GAT GGG CTC CTC TCG 673
Met Tyr Ser Thr Ala Ala Gln Gln His Gln Trp Asp Gly Leu Leu Ser
205 210 215

TAT CAG GAC TCT CTG GGC TGC CGA CTG GTG TTC CTG CTC ATG CAA TAC 721
Tyr Gln Asp Ser Leu Gly Cys Arg Leu Val Phe Leu Leu Met Gln Tyr
220 225 230 235

TGC GTG GCG GCC AAC TAC TAC TGG TTG CTG GTG GAA GGC GTG TAT CTG 769
Cys Val Ala Ala Asn Tyr Tyr Trp Leu Leu Val Glu Gly Val Tyr Leu
240 245 250

TAC ACA CTG CTG GCC TTC TCG GTG TTC TCG GAG CAG CGC ATC TTC AAG 817
Tyr Thr Leu Leu Ala Phe Ser Val Phe Ser Glu Gln Arg Ile Phe Lys
255 260 265

CTG TAC CTG AGC ATA GGC TGG GGA GTT CCG CTG CTG TTC GTT ATC CCC 865
Leu Tyr Leu Ser Ile Gly Trp Gly Val Pro Leu Leu Phe Val Ile Pro
270 275 280

TGG GGC ATT GTC AAG TAT CTC TAC GAG GAC GAG GGT TGC TGG ACC AGG 913
Trp Gly Ile Val Lys Tyr Leu Tyr Glu Asp Glu Gly Cys Trp Thr Arg
285 290 295

AAC TCC AAC ATG AAC TAT TGG CTC ATC ATA CGC TTG CCC ATT CTC TTT 961
Asn Ser Asn Met Asn Tyr Trp Leu Ile Ile Arg Leu Pro Ile Leu Phe
300 305 310 315

GCA ATC GGG GTC AAC TTC CTT GTC TTC ATC CGG GTC ATC TGC ATC GTG 1009
Ala Ile Gly Val Asn Phe Leu Val Phe Ile Arg Val Ile Cys Ile Val
320 325 330

ATA GCC AAG CTG AAG GCT AAT CTC ATG TGT AAG ACC GAC ATC AAA TGC 1057
Ile Ala Lys Leu Lys Ala Asn Leu Met Cys Lys Thr Asp Ile Lys Cys
335 340 345

AGA CTC GCG AAG TCC ACT CTG ACG CTC ATC CCG CTT CTG GGC ACG CAT 1105
Arg Leu Ala Lys Ser Thr Leu Thr Leu Ile Pro Leu Leu Gly Thr His
350 355 360

GAA GTC ATC TTT GCC TTT GTG ATG GAC GAG CAC GCC CGA GGA ACC CTA 1153
Glu Val Ile Phe Ala Phe Val Met Asp Glu His Ala Arg Gly Thr Leu
365 370 375

CGC TTC GTC AAG CTG TTC ACA GAG CTC TCC TTC ACT TCC TTC CAG GGC 1201
Arg Phe Val Lys Leu Phe Thr Glu Leu Ser Phe Thr Ser Phe Gln Gly
380 385 390 395

TTT ATG GTG GCT GTC TTG TAC TGC TTT GTC AAC AAT GAG GTC CAG ATG 1249
Phe Met Val Ala Val Leu Tyr Cys Phe Val Asn Asn Glu Val Gln Met
400 405 410

GAG TTT CGG AAG AGC TGG GAG CGC TGG AGG CTG GAG CGC TTG AAC ATC 1297
Glu Phe Arg Lys Ser Trp Glu Arg Trp Arg Leu Glu Arg Leu Asn Ile
415 420 425

-continued

```
CAG AGG GAC AGC AGC ATG AAA CCC CTC AAG TGT CCC ACC AGC AGC GTC      1345
Gln Arg Asp Ser Ser Met Lys Pro Leu Lys Cys Pro Thr Ser Ser Val
        430                 435                 440

AGC AGT GGG GCC ACG GTG GGC AGC AGC GTG TAT GCA GCC ACC TGC CAA      1393
Ser Ser Gly Ala Thr Val Gly Ser Ser Val Tyr Ala Ala Thr Cys Gln
    445                 450                 455

AAT TCC TGC AGC TGAGCCCCAG TGCTGCGCTT CCTGATGGTC CTTGCTGCTG          1445
Asn Ser Cys Ser
460

GCTGGGTGGC CATCCCAGGT GGGAGAGACC CTGGGGACAG GGAATATGAG GGATACAGGC    1505

ACATGTGTGT GCGTGCCCGC ACACCACACA CACACACACA CACACACACA CACACACACA    1565

CACACACACA CACACGCTTT CCTCCTCAAA CCTATCAAAC AGGCATCGGC ATCGGCAGTG    1625

CCTCCTGGGA CCACAGACAC ATGTTCTCCA AGGAGAACAG CCTGCTAATT TAATCTCAGG    1685

CGACAGGAAG AGAGGAAGAA ACAATTGCTG TTAAGACGAG GAGGACTTCT TCCTGTTAAA    1745

GCTGCAAGGC CCTTGGGGTT CCCTCGGACA GAACTGCAAA TCAACCCCGG AACTCTCGCT    1805

CAAGGGCAAT TGCTGACGGG TGGAACTTGG GCTTGCGAGA GGAGGCAGGT CCATGAGAGA    1865

CCTGCCCTTG GAACCTCAGC CAGCACAGCG CTCATCAAGG TGAGCTGGCT GTGCTGTGTG    1925

CACGGCTGGG GTTGTCACCT ACATCAGCCT TCCTCTCGGA CAAGAGGCTT TTCTCTGTGC    1985

ATCTGGAGTG CCGCCATTCC TCCATCTGCC CGTTCATCCG CCATCCTGTC TTTGCCTTGG    2045

GGAGGGGGAG GTTTGTTGAA GTCATGCCGT GCAGCTCTTT CTGGAAATAT CTGTGGATGG    2105

TGTTGAAGAT AAGCATGGGG GAGATACAAC AGAGGCAGTC TTTGCCCATG GCCACTTCTT    2165

GCCTGGTCCT TTAAGCCACT TTGCTGCTTG GTTTCTGCCC TGCATGGGTA CTACTAGGGC    2225

AGGTCCCAAG TTGAGAAGCC CAGAGGTGAG GTGTGAACCC TCAGTTCTGT TGTAAAGATG    2285

CTCAAATACC CTCTAAGGTT CATCTAAAGG AGTAACCTGC CTAGGGGTGC TGTTGACCTG    2345

AAATCAAGAG GACCAAAGGA TCCATTGCCA ACACCCCCCA TCCCCCACAC ACACCTCATC    2405

TGTGACCAGA GTCTATGCTT TGAATCAGAA TGGGCTATAT CCTCTGACCT CAGAGGCTAT    2465

GACCCAGAAG AGATTCTTCC CTGAATCCTC CCACTTTGCA CACATATAGA CTTTATCCTT    2525

CTTCACTCTG TGTCTATTCA AACGTATAAT TCTGGTTTCT CTCACCCCAC GGAAGAACTA    2585

GATCACAGCA ACTGTTATGT TTGAGGGAGT GGGGGAGAAG GTGATTGATT TGACCCCCTC    2645

TCCCCCACCG GTGTTGATAA GTAGCGTCTG TCCCACCTCC AGACTCCACC CACACATAAT    2705

GAGCAGCACA TAGACCAGGA TGGGGGGGGT GGTATATCAT GCTTGCCCTC CTCCAACCAC    2765

TATGAGAAGG CTAGCAGAAG ACACCACTGC ACAGACCCAA GTCCAAGGAC TGCCTCCCAG    2825

GGAATTAGGC AGTGACTTCC TAGAGGCCAA GAAAGACTCC AAGAGCTGGA GAAGAATCCT    2885

AGTCGATCTG GATCTCTTTT GAGGTTGGGG TTGGGGTGGC TTTCAATGGA TTCTCTCATG    2945

AGGCTTATCT CTCCCTCATC CCGTGGAGAG TGGGGGACCC TCCCTAGTGC TCACACTAGA    3005

CACTGTGCCC CTTGGAGAGG CATAAGGCAT GTATGGGAGA TAATAATGGG CTATAAAACA    3065

T                                                                    3066
```

( 2 ) INFORMATION FOR SEQ ID NO:2:

( i ) SEQUENCE CHARACTERISTICS:
( A ) LENGTH: 463 amino acids
( B ) TYPE: amino acid
( D ) TOPOLOGY: linear ( i i ) MOLECULE TYPE: protein ( x i ) SEQUENCE DESCRIPTION: SEQ ID NO:2:

-continued

| | | | | | | | | | | | | | | | |
|---|---|---|---|---|---|---|---|---|---|---|---|---|---|---|---|
| Met | Ala | Val | Thr | Pro | Ser | Leu | Leu | Arg | Leu | Ala | Leu | Leu | Leu | Leu | Gly |
| 1 | | | | 5 | | | | | 10 | | | | | 15 | |
| Ala | Val | Gly | Arg | Ala | Gly | Pro | Arg | Pro | Gln | Gly | Ala | Thr | Val | Ser | Leu |
| | | | 20 | | | | | 25 | | | | | 30 | | |
| Ser | Glu | Thr | Val | Gln | Lys | Trp | Arg | Glu | Tyr | Arg | His | Gln | Cys | Gln | Arg |
| | | 35 | | | | | 40 | | | | | 45 | | | |
| Phe | Leu | Thr | Glu | Ala | Pro | Leu | Leu | Ala | Thr | Gly | Leu | Phe | Cys | Asn | Arg |
| | 50 | | | | | 55 | | | | | 60 | | | | |
| Thr | Phe | Asp | Asp | Tyr | Ala | Cys | Trp | Pro | Asp | Gly | Pro | Pro | Gly | Ser | Phe |
| 65 | | | | | 70 | | | | | 75 | | | | | 80 |
| Val | Asn | Val | Ser | Cys | Pro | Trp | Tyr | Leu | Pro | Trp | Ala | Ser | Ser | Val | Leu |
| | | | | 85 | | | | | 90 | | | | | 95 | |
| Gln | Gly | His | Val | Tyr | Arg | Phe | Cys | Thr | Ala | Glu | Gly | Ile | Trp | Leu | His |
| | | | 100 | | | | | 105 | | | | | 110 | | |
| Lys | Asp | Asn | Ser | Ser | Leu | Pro | Trp | Arg | Asp | Leu | Ser | Glu | Cys | Glu | Glu |
| | | 115 | | | | | 120 | | | | | 125 | | | |
| Ser | Lys | Gln | Gly | Glu | Arg | Asn | Ser | Pro | Glu | Glu | Gln | Leu | Leu | Ser | Leu |
| | 130 | | | | | 135 | | | | | 140 | | | | |
| Tyr | Ile | Ile | Tyr | Thr | Val | Gly | Tyr | Ala | Leu | Ser | Phe | Ser | Ala | Leu | Val |
| 145 | | | | | 150 | | | | | 155 | | | | | 160 |
| Ile | Ala | Ser | Ala | Ile | Leu | Val | Ser | Phe | Arg | His | Leu | His | Cys | Thr | Arg |
| | | | | 165 | | | | | 170 | | | | | 175 | |
| Asn | Tyr | Ile | His | Leu | Asn | Leu | Phe | Ala | Ser | Phe | Ile | Leu | Arg | Ala | Leu |
| | | | 180 | | | | | 185 | | | | | 190 | | |
| Ser | Val | Phe | Ile | Lys | Asp | Ala | Ala | Leu | Lys | Trp | Met | Tyr | Ser | Thr | Ala |
| | | 195 | | | | | 200 | | | | | 205 | | | |
| Ala | Gln | Gln | His | Gln | Trp | Asp | Gly | Leu | Leu | Ser | Tyr | Gln | Asp | Ser | Leu |
| | 210 | | | | | 215 | | | | | 220 | | | | |
| Gly | Cys | Arg | Leu | Val | Phe | Leu | Leu | Met | Gln | Tyr | Cys | Val | Ala | Ala | Asn |
| 225 | | | | | 230 | | | | | 235 | | | | | 240 |
| Tyr | Tyr | Trp | Leu | Leu | Val | Glu | Gly | Val | Tyr | Leu | Tyr | Thr | Leu | Leu | Ala |
| | | | | 245 | | | | | 250 | | | | | 255 | |
| Phe | Ser | Val | Phe | Ser | Glu | Gln | Arg | Ile | Phe | Lys | Leu | Tyr | Leu | Ser | Ile |
| | | | 260 | | | | | 265 | | | | | 270 | | |
| Gly | Trp | Gly | Val | Pro | Leu | Leu | Phe | Val | Ile | Pro | Trp | Gly | Ile | Val | Lys |
| | | 275 | | | | | 280 | | | | | 285 | | | |
| Tyr | Leu | Tyr | Glu | Asp | Glu | Gly | Cys | Trp | Thr | Arg | Asn | Ser | Asn | Met | Asn |
| | 290 | | | | | 295 | | | | | 300 | | | | |
| Tyr | Trp | Leu | Ile | Ile | Arg | Leu | Pro | Ile | Leu | Phe | Ala | Ile | Gly | Val | Asn |
| 305 | | | | | 310 | | | | | 315 | | | | | 320 |
| Phe | Leu | Val | Phe | Ile | Arg | Val | Ile | Cys | Ile | Val | Ile | Ala | Lys | Leu | Lys |
| | | | | 325 | | | | | 330 | | | | | 335 | |
| Ala | Asn | Leu | Met | Cys | Lys | Thr | Asp | Ile | Lys | Cys | Arg | Leu | Ala | Lys | Ser |
| | | | 340 | | | | | 345 | | | | | 350 | | |
| Thr | Leu | Thr | Leu | Ile | Pro | Leu | Leu | Gly | Thr | His | Glu | Val | Ile | Phe | Ala |
| | | 355 | | | | | 360 | | | | | 365 | | | |
| Phe | Val | Met | Asp | Glu | His | Ala | Arg | Gly | Thr | Leu | Arg | Phe | Val | Lys | Leu |
| | 370 | | | | | 375 | | | | | 380 | | | | |
| Phe | Thr | Glu | Leu | Ser | Phe | Thr | Ser | Phe | Gln | Gly | Phe | Met | Val | Ala | Val |
| 385 | | | | | 390 | | | | | 395 | | | | | 400 |
| Leu | Tyr | Cys | Phe | Val | Asn | Asn | Glu | Val | Gln | Met | Glu | Phe | Arg | Lys | Ser |
| | | | | 405 | | | | | 410 | | | | | 415 | |
| Trp | Glu | Arg | Trp | Arg | Leu | Glu | Arg | Leu | Asn | Ile | Gln | Arg | Asp | Ser | Ser |
| | | | 420 | | | | | 425 | | | | | 430 | | |

-continued

Met Lys Pro Leu Lys Cys Pro Thr Ser Ser Val Ser Ser Gly Ala Thr
435 440 445

Val Gly Ser Ser Val Tyr Ala Ala Thr Cys Gln Asn Ser Cys Ser
450 455 460

( 2 ) INFORMATION FOR SEQ ID NO:3:

( i ) SEQUENCE CHARACTERISTICS:
( A ) LENGTH: 1909 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( v i ) ORIGINAL SOURCE:
( A ) ORGANISM: Homo sapiens ( i x ) FEATURE:
( A ) NAME/KEY: CDS
( B ) LOCATION: 3..887

( x i ) SEQUENCE DESCRIPTION: SEQ ID NO:3:

TC AGA CAC CTG TAC TGC ACC AGG AAC TAC ATC CAC CTG AAC CTG TTT 47
Arg His Leu Tyr Cys Thr Arg Asn Tyr Ile His Leu Asn Leu Phe
1 5 10 15

GCA TCC TTC ATC CTG CGA GCA TTG TCC GTC TTC ATC AAG GAC GCA GCC 95
Ala Ser Phe Ile Leu Arg Ala Leu Ser Val Phe Ile Lys Asp Ala Ala
20 25 30

CTG AAG TGG ATG TAT AGC ACA GCC GCC CAG CAG CAC CAG TGG GAT GGG 143
Leu Lys Trp Met Tyr Ser Thr Ala Ala Gln Gln His Gln Trp Asp Gly
35 40 45

CTC CTC TCC TAC CAG GAC TCT CTG AGC TGC CGC CTG GTG TTT CTG CTC 191
Leu Leu Ser Tyr Gln Asp Ser Leu Ser Cys Arg Leu Val Phe Leu Leu
50 55 60

ATG CAG TAC TGT GTG GCG GCC AAT TAC TAC TGG CTC TTG GTG GAG GGC 239
Met Gln Tyr Cys Val Ala Ala Asn Tyr Tyr Trp Leu Leu Val Glu Gly
65 70 75

GTG TAC CTG TAC ACA CTG CTG GCC TTC TCG GTG TTC TCT GAG CAA TGG 287
Val Tyr Leu Tyr Thr Leu Leu Ala Phe Ser Val Phe Ser Glu Gln Trp
80 85 90 95

ATC TTC AGG CTC TAC GTG AGC ATA GGC TGG GGT GTT CCC CTG CTG TTT 335
Ile Phe Arg Leu Tyr Val Ser Ile Gly Trp Gly Val Pro Leu Leu Phe
100 105 110

GTT GTC CCC TGG GGC ATT GTC AAG ATC CTC TAT GAG GAC GAG GGC TGC 383
Val Val Pro Trp Gly Ile Val Lys Ile Leu Tyr Glu Asp Glu Gly Cys
115 120 125

TGG ACC AGG AAC TCC AAC ATG AAC TAC TGG CTC ATT ATC CGG CTG CCC 431
Trp Thr Arg Asn Ser Asn Met Asn Tyr Trp Leu Ile Ile Arg Leu Pro
130 135 140

ATT CTC TTT GCC ATT GGG GTG AAC TTC CTC ATC TTT GTT CGG GTC ATC 479
Ile Leu Phe Ala Ile Gly Val Asn Phe Leu Ile Phe Val Arg Val Ile
145 150 155

TGC ATC GTG GTA TCC AAA CTG AAG GCC AAT GTC ATG TGC AAG ACA GAC 527
Cys Ile Val Val Ser Lys Leu Lys Ala Asn Val Met Cys Lys Thr Asp
160 165 170 175

ATC AAA TGC AGA CTT GCC AAG TCC ACG CTG ACA CTC ATC CCC CTG CTG 575
Ile Lys Cys Arg Leu Ala Lys Ser Thr Leu Thr Leu Ile Pro Leu Leu
180 185 190

GGG ACT CAT GAG GTC ATC TTT GCC TTT GTG ATG GAC GAG CAC GCC CGG 623
Gly Thr His Glu Val Ile Phe Ala Phe Val Met Asp Glu His Ala Arg
195 200 205

-continued

```
GGG ACC CTG CGC TTC ATC AAG CTG TTT ACA GAG CTC TCC TTC ACC TCC       671
Gly Thr Leu Arg Phe Ile Lys Leu Phe Thr Glu Leu Ser Phe Thr Ser
        210                 215                 220

TTC CAG GGG CTG ATG GTG GCC ATC TTA TAC TGC TTT GTC AAC AAT GAG       719
Phe Gln Gly Leu Met Val Ala Ile Leu Tyr Cys Phe Val Asn Asn Glu
    225                 230                 235

GTC CAG CTG GAA TTT CGG AAG AGC TGG GAG CGC TGG CGG CTT GAG CAC       767
Val Gln Leu Glu Phe Arg Lys Ser Trp Glu Arg Trp Arg Leu Glu His
240                 245                 250                 255

TTG CAC ATC CAG AGG GAC AGC AGC ATG AAG CCC CTC AAG TGT CCC ACC       815
Leu His Ile Gln Arg Asp Ser Ser Met Lys Pro Leu Lys Cys Pro Thr
                260                 265                 270

AGC AGC CTG AGC AGT GGA GCC ACG GCG GGC AGC AGC ATG TAC ACA GCC       863
Ser Ser Leu Ser Ser Gly Ala Thr Ala Gly Ser Ser Met Tyr Thr Ala
            275                 280                 285

ACT TGC CAG GCC TCC TGC AGC TGAGACTCCA GCGCCTGCCC TCCCTGGGGT          914
Thr Cys Gln Ala Ser Cys Ser
        290

CCTTGCTGCG GCCGGGTGGC AATCCAGGAG AAGCAGCCTC CTAATTTGAT CACAGTGGCG     974

AGAGGAGAGG AAAAACGATC GCTGTGAAAA TGAGGAGGAT TGCTTCTTGT GAAACCACAG    1034

GCCCTTGGGG TTCCCCCAGA CAGAGCCGCA AATCAACCCC AGACTCAAAC TCAAGGTCAA    1094

CGGCTTATTA GTGAAACTGG GGCTTGCAAG AGGAGGTGGT TCTGAAAGTG GCTCTTCTAA    1154

CCTCAGCCAA ACACGAGCGG GAGTGACGGG AGCCTCCTCT GCTTGCATCA CTTGGGGTCA    1214

CCACCCTCCC CTGTCTTCTC TCAAAGGGAA GCTGTTTGTG TGTCTGGGTT GCTTATTTCC    1274

CTCATCTTGC CCCCTCATCT CACTGCCCAG TTTCTTTTTG AGGGCTTGTT GGCCACTGCC    1334

AGCAGCTGTT TCTGGAAATG GCTGTAGGTG GTGTTGAGAA AGAATGAGCA TTGAGACACG    1394

GTGCTCGCTT CTCCTCCAGG TATTTGAGTT GTTTTGGTGC CTGCCTCTGC CATGCCCAGA    1454

GAATCAGGGC AGGCTTGCCA CCGGGGAACC CAGCCCTGGG GTATGAGCTG CCAAGTCTAT    1514

TTTAAAGACG CTCAAGAATC CTCTGGGGTT CATCTAGGGA CACGTTAGGA ATGTCCAGAC    1574

TGTGGGTGTA GGTTACCTGC CACTTCCAGG ACGCAGAGGG CCAAGAGAGA CATTGCCTCC    1634

ACCTCTCCTG AATACTTATC TGTGACCACA CGCTGTCTCT TGAGATTTGG ATACACTCTC    1694

TAGCTTTAGG GGACCATGAA GAGACTCTCT TAGGAAACCA ATAGTCCCCA TCAGCACCAT    1754

GGAGGCAGGC TCCCCCTGCC TTTGAAATTC CCCCACTTGG GAGCTGATAT ACTTCACTCA    1814

CTTTTCTTTA TTGCTGTGAT AGTCTGTGTG CACAATGGGC AATTCTGACT TCTCCCATCT    1874

AGTGAAATGA GCGAAATCAT GGTTGTAGTG ATCTT                                1909
```

( 2 ) INFORMATION FOR SEQ ID NO:4:

( i ) SEQUENCE CHARACTERISTICS:
( A ) LENGTH: 294 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Arg His Leu Tyr Cys Thr Arg Asn Tyr Ile His Leu Asn Leu Phe Ala
 1               5                  10                  15

Ser Phe Ile Leu Arg Ala Leu Ser Val Phe Ile Lys Asp Ala Ala Leu
            20                  25                  30

Lys Trp Met Tyr Ser Thr Ala Ala Gln Gln His Gln Trp Asp Gly Leu
        35                  40                  45
```

-continued

```
Leu Ser Tyr Gln Asp Ser Leu Ser Cys Arg Leu Val Phe Leu Leu Met
     50                  55                  60

Gln Tyr Cys Val Ala Ala Asn Tyr Tyr Trp Leu Leu Val Glu Gly Val
 65                  70                  75                      80

Tyr Leu Tyr Thr Leu Leu Ala Phe Ser Val Phe Ser Glu Gln Trp Ile
                 85                  90                      95

Phe Arg Leu Tyr Val Ser Ile Gly Trp Gly Val Pro Leu Leu Phe Val
            100                 105                 110

Val Pro Trp Gly Ile Val Lys Ile Leu Tyr Glu Asp Glu Gly Cys Trp
        115                 120                 125

Thr Arg Asn Ser Asn Met Asn Tyr Trp Leu Ile Ile Arg Leu Pro Ile
    130                 135                 140

Leu Phe Ala Ile Gly Val Asn Phe Leu Ile Phe Val Arg Val Ile Cys
145                 150                 155                 160

Ile Val Val Ser Lys Leu Lys Ala Asn Val Met Cys Lys Thr Asp Ile
                165                 170                 175

Lys Cys Arg Leu Ala Lys Ser Thr Leu Thr Leu Ile Pro Leu Leu Gly
            180                 185                 190

Thr His Glu Val Ile Phe Ala Phe Val Met Asp Glu His Ala Arg Gly
        195                 200                 205

Thr Leu Arg Phe Ile Lys Leu Phe Thr Glu Leu Ser Phe Thr Ser Phe
    210                 215                 220

Gln Gly Leu Met Val Ala Ile Leu Tyr Cys Phe Val Asn Asn Glu Val
225                 230                 235                 240

Gln Leu Glu Phe Arg Lys Ser Trp Glu Arg Trp Arg Leu Glu His Leu
                245                 250                 255

His Ile Gln Arg Asp Ser Ser Met Lys Pro Leu Lys Cys Pro Thr Ser
            260                 265                 270

Ser Leu Ser Ser Gly Ala Thr Ala Gly Ser Ser Met Tyr Thr Ala Thr
        275                 280                 285

Cys Gln Ala Ser Cys Ser
    290
```

( 2 ) INFORMATION FOR SEQ ID NO: 5:

( i ) SEQUENCE CHARACTERISTICS:
( A ) LENGTH: 449 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i i i ) ANTI-SENSE: NO ( v i ) ORIGINAL SOURCE:
( A ) ORGANISM: Rattus norvegicus
( B ) STRAIN: Sprague-Dawley ( x i ) SEQUENCE DESCRIPTION: SEQ ID NO: 5:

```
Met Leu Ser Thr Met Arg Pro Arg Leu Ser Leu Leu Leu Leu Arg Leu
1               5                   10                  15

Leu Leu Leu Thr Lys Ala Ala His Thr Val Gly Val Pro Pro Arg Leu
            20                  25                  30

Cys Asp Val Arg Arg Val Leu Leu Glu Glu Arg Ala His Cys Leu Gln
        35                  40                  45

Gln Leu Ser Lys Glu Lys Lys Gly Ala Leu Gly Pro Glu Thr Ala Ser
    50                  55                  60
```

-continued

Gly Cys Glu Gly Leu Trp Asp Asn Met Ser Cys Trp Pro Ser Ser Ala
65 70 75 80

Pro Ala Arg Thr Val Glu Val Gln Cys Pro Lys Phe Leu Leu Met Leu
85 90 95

Ser Asn Lys Asn Gly Ser Leu Phe Arg Asn Cys Thr Gln Asp Gly Trp
100 105 110

Ser Glu Thr Phe Pro Arg Pro Asp Leu Ala Cys Gly Val Asn Ile Asn
115 120 125

Asn Ser Phe Asn Glu Arg Arg His Ala Tyr Leu Leu Lys Leu Lys Val
130 135 140

Met Tyr Thr Val Gly Tyr Ser Ser Ser Leu Ala Met Leu Leu Val Ala
145 150 155 160

Leu Ser Ile Leu Cys Ser Phe Arg Arg Leu His Cys Thr Arg Asn Tyr
165 170 175

Ile His Met His Leu Phe Val Ser Phe Ile Leu Arg Ala Leu Ser Asn
180 185 190

Phe Ile Lys Asp Ala Val Leu Phe Ser Ser Asp Asp Val Thr Tyr Cys
195 200 205

Asp Ala His Lys Val Gly Cys Lys Leu Val Met Ile Phe Phe Gln Tyr
210 215 220

Cys Ile Met Ala Asn Tyr Ala Trp Leu Leu Val Glu Gly Leu Tyr Leu
225 230 235 240

His Thr Leu Leu Ala Ile Ser Phe Phe Ser Glu Arg Lys Tyr Leu Gln
245 250 255

Ala Phe Val Leu Leu Gly Trp Gly Ser Pro Ala Ile Phe Val Ala Leu
260 265 270

Trp Ala Ile Thr Arg His Phe Leu Glu Asn Thr Gly Cys Trp Asp Ile
275 280 285

Asn Ala Asn Ala Ser Val Trp Trp Val Ile Arg Gly Pro Val Ile Leu
290 295 300

Ser Ile Leu Ile Asn Phe Ile Phe Phe Ile Asn Ile Leu Arg Ile Leu
305 310 315 320

Met Arg Lys Leu Arg Thr Gln Glu Thr Arg Gly Ser Glu Thr Asn His
325 330 335

Tyr Lys Arg Leu Ala Lys Ser Thr Leu Leu Leu Ile Pro Leu Phe Gly
340 345 350

Ile His Tyr Ile Val Phe Ala Phe Ser Pro Glu Asp Ala Met Glu Val
355 360 365

Gln Leu Phe Phe Glu Leu Ala Leu Gly Ser Phe Gln Gly Leu Val Val
370 375 380

Ala Val Leu Tyr Cys Phe Leu Asn Gly Glu Val Gln Leu Glu Val Gln
385 390 395 400

Lys Lys Trp Arg Gln Trp His Leu Gln Glu Phe Pro Leu Arg Pro Val
405 410 415

Ala Phe Asn Asn Ser Phe Ser Asn Ala Thr Asn Gly Pro Thr His Ser
420 425 430

Thr Lys Ala Ser Thr Glu Gln Ser Arg Ser Ile Pro Arg Ala Ser Ile
435 440 445

Ile ( 2 ) INFORMATION FOR SEQ ID NO: 6:

( i ) SEQUENCE CHARACTERISTICS:

( A ) LENGTH: 585 amino acids

-continued ( B ) TYPE: amino acid
( C ) STRANDEDNESS: single
( D ) TOPOLOGY: linear ( i i ) MOLECULE TYPE: protein ( i i i ) HYPOTHETICAL: NO ( i i i ) ANTI-SENSE: NO ( v i ) ORIGINAL SOURCE:
( A ) ORGANISM: Didelphis virginiana ( x i ) SEQUENCE DESCRIPTION: SEQ ID NO: 6:

Met Gly Ala Pro Arg Ile Ser His Ser Leu Ala Leu Leu Leu Cys Cys
1 5 10 15

Ser Val Leu Ser Ser Val Tyr Ala Leu Val Asp Ala Asp Asp Val Ile
20 25 30

Thr Lys Glu Glu Gln Ile Ile Leu Leu Arg Asn Ala Gln Ala Gln Cys
35 40 45

Glu Gln Arg Leu Lys Glu Val Leu Arg Val Pro Glu Leu Ala Glu Ser
50 55 60

Ala Lys Asp Trp Met Ser Arg Ser Ala Lys Thr Lys Lys Glu Lys Pro
65 70 75 80

Ala Glu Lys Leu Tyr Ser Gln Ala Glu Glu Ser Arg Glu Val Ser Asp
85 90 95

Arg Ser Arg Leu Gln Asp Gly Phe Cys Leu Pro Glu Trp Asp Asn Ile
100 105 110

Val Cys Trp Pro Ala Gly Val Pro Gly Lys Val Val Ala Val Pro Cys
115 120 125

Pro Asp Tyr Ile Tyr Asp Phe Asn His Lys Gly Arg Ala Tyr Arg Arg
130 135 140

Cys Asp Ser Asn Gly Ser Trp Glu Leu Val Pro Gly Asn Asn Arg Thr
145 150 155 160

Trp Ala Asn Tyr Ser Glu Cys Val Lys Phe Leu Thr Asn Glu Thr Arg
165 170 175

Glu Arg Glu Val Phe Asp Arg Leu Gly Met Ile Tyr Thr Val Gly Tyr
180 185 190

Ser Ile Ser Leu Gly Ser Leu Thr Val Ala Val Leu Ile Leu Gly Tyr
195 200 205

Phe Arg Arg Leu His Cys Thr Arg Asn Tyr Ile His Met His Leu Phe
210 215 220

Val Ser Phe Met Leu Arg Ala Val Ser Ile Phe Ile Lys Asp Ala Val
225 230 235 240

Leu Tyr Ser Gly Val Ser Thr Asp Glu Ile Glu Arg Ile Thr Glu Glu
245 250 255

Glu Leu Arg Ala Phe Thr Glu Pro Pro Pro Ala Asp Lys Ala Gly Phe
260 265 270

Val Gly Cys Arg Val Ala Val Thr Val Phe Leu Tyr Phe Leu Thr Thr
275 280 285

Asn Tyr Tyr Trp Ile Leu Val Glu Gly Leu Tyr Leu His Ser Leu Ile
290 295 300

Phe Met Ala Phe Phe Ser Glu Lys Lys Tyr Leu Trp Gly Phe Thr Leu
305 310 315 320

Phe Gly Trp Gly Leu Pro Ala Val Phe Val Ala Val Trp Val Thr Val
325 330 335

Arg Ala Thr Leu Ala Asn Thr Glu Cys Trp Asp Leu Ser Ser Gly Asn
340 345 350

-continued

Lys Lys Trp Ile Ile Gln Val Pro Ile Leu Ala Ala Ile Val Val Asn
355 360 365

Phe Ile Leu Phe Ile Asn Ile Ile Arg Val Leu Ala Thr Lys Leu Arg
370 375 380

Glu Thr Asn Ala Gly Arg Cys Asp Thr Arg Gln Gln Tyr Arg Lys Leu
385 390 395 400

Leu Lys Ser Thr Leu Val Leu Met Pro Leu Phe Gly Val His Tyr Ile
405 410 415

Val Phe Met Ala Thr Pro Tyr Thr Glu Val Ser Gly Ile Leu Trp Gln
420 425 430

Val Gln Met His Tyr Glu Met Leu Phe Asn Ser Phe Gln Gly Phe Phe
435 440 445

Val Ala Ile Ile Tyr Cys Phe Cys Asn Gly Glu Val Gln Ala Glu Ile
450 455 460

Lys Lys Ser Trp Ser Arg Trp Thr Leu Ala Leu Asp Phe Lys Arg Lys
465 470 475 480

Ala Arg Ser Gly Ser Ser Thr Tyr Ser Tyr Gly Pro Met Val Ser His
485 490 495

Thr Ser Val Thr Asn Val Gly Pro Arg Gly Gly Leu Ala Leu Ser Leu
500 505 510

Ser Pro Arg Leu Ala Pro Gly Ala Gly Ala Ser Ala Asn Gly His His
515 520 525

Gln Leu Pro Gly Tyr Val Lys His Gly Ser Ile Ser Glu Asn Ser Leu
530 535 540

Pro Ser Ser Gly Pro Glu Pro Gly Thr Lys Asp Asp Gly Tyr Leu Asn
545 550 555 560

Gly Ser Gly Leu Tyr Glu Pro Met Val Gly Glu Gln Pro Pro Pro Leu
565 570 575

Leu Glu Glu Glu Arg Glu Thr Val Met
580 585

( 2 ) INFORMATION FOR SEQ ID NO: 7:

( i ) SEQUENCE CHARACTERISTICS:
( A ) LENGTH: 482 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i i i ) ANTI-SENSE: NO ( v i ) ORIGINAL SOURCE:
( A ) ORGANISM: Sus scrofa ( x i ) SEQUENCE DESCRIPTION: SEQ ID NO: 7:

Met Arg Phe Thr Leu Thr Arg Trp Cys Leu Thr Leu Phe Ile Phe Leu
1 5 10 15

Asn Arg Pro Leu Pro Val Leu Pro Asp Ser Ala Asp Gly Ala His Thr
20 25 30

Pro Thr Leu Glu Pro Glu Pro Phe Leu Tyr Ile Leu Gly Lys Gln Arg
35 40 45

Met Leu Glu Ala Gln His Arg Cys Tyr Asp Arg Met Gln Lys Leu Pro
50 55 60

Pro Tyr Gln Gly Glu Gly Leu Tyr Cys Asn Arg Thr Trp Asp Gly Trp
65 70 75 80

-continued

Ser Cys Trp Asp Asp Thr Pro Ala Gly Val Leu Ala Glu Gln Tyr Cys
85 90 95

Pro Asp Tyr Phe Pro Asp Phe Asp Ala Ala Glu Lys Val Thr Lys Tyr
100 105 110

Cys Gly Glu Asp Gly Asp Trp Tyr Arg His Pro Glu Ser Asn Ile Ser
115 120 125

Trp Ser Asn Tyr Thr Met Cys Asn Ala Phe Thr Pro Asp Lys Leu Gln
130 135 140

Asn Ala Tyr Ile Leu Tyr Tyr Leu Ala Ile Val Gly His Ser Leu Ser
145 150 155 160

Ile Leu Thr Leu Leu Ile Ser Leu Gly Ile Phe Met Phe Leu Arg Ser
165 170 175

Ile Ser Cys Gln Arg Val Thr Leu His Lys Asn Met Phe Leu Thr Tyr
180 185 190

Val Leu Asn Ser Ile Ile Ile Ile Val His Leu Val Val Ile Val Pro
195 200 205

Asn Gly Glu Leu Val Lys Arg Asp Pro Pro Ile Cys Lys Val Leu His
210 215 220

Phe Phe His Gln Tyr Met Met Ser Cys Asn Tyr Phe Trp Met Leu Cys
225 230 235 240

Glu Gly Val Tyr Leu His Thr Leu Ile Val Val Ser Val Phe Ala Glu
245 250 255

Gly Gln Arg Leu Trp Trp Tyr His Val Leu Gly Trp Gly Phe Pro Leu
260 265 270

Ile Pro Thr Thr Ala His Ala Ile Thr Arg Ala Val Leu Phe Asn Asp
275 280 285

Asn Cys Trp Leu Ser Val Asp Thr Asn Leu Leu Tyr Ile Ile His Gly
290 295 300

Pro Val Met Ala Ala Leu Val Val Asn Phe Phe Phe Leu Leu Asn Ile
305 310 315 320

Leu Arg Val Leu Val Lys Lys Leu Lys Glu Ser Gln Glu Ala Glu Ser
325 330 335

His Met Tyr Leu Lys Ala Val Arg Ala Thr Leu Ile Leu Val Pro Leu
340 345 350

Leu Gly Val Gln Phe Val Val Leu Pro Trp Arg Pro Ser Thr Pro Leu
355 360 365

Leu Gly Lys Ile Tyr Asp Tyr Val Val His Ser Leu Ile His Phe Gln
370 375 380

Gly Phe Phe Val Ala Ile Ile Tyr Cys Phe Cys Asn His Glu Val Gln
385 390 395 400

Gly Ala Leu Lys Arg Gln Trp Asn Gln Tyr Gln Ala Gln Arg Trp Ala
405 410 415

Gly Arg Arg Ser Thr Arg Ala Ala Asn Ala Ala Ala Ala Thr Ala Ala
420 425 430

Ala Ala Ala Ala Leu Ala Glu Thr Val Glu Ile Pro Val Tyr Ile Cys
435 440 445

His Gln Glu Pro Arg Glu Glu Pro Ala Gly Glu Glu Pro Val Val Glu
450 455 460

Val Glu Gly Val Glu Val Ile Ala Met Glu Val Leu Glu Gln Glu Thr
465 470 475 480

Ser Ala ( 2 ) INFORMATION FOR SEQ ID NO: 8:

-continued ( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i i i ) ANTI-SENSE: NO ( v i ) ORIGINAL SOURCE:
( A ) ORGANISM: Homo sapiens ( x i ) SEQUENCE DESCRIPTION: SEQ ID NO: 8:

Arg Leu Ala Lys
1

( 2 ) INFORMATION FOR SEQ ID NO: 9:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i i i ) ANTI-SENSE: NO ( v i ) ORIGINAL SOURCE:
( A ) ORGANISM: Homo sapiens ( x i ) SEQUENCE DESCRIPTION: SEQ ID NO: 9:

Lys Ala Leu Lys
1

METHOD FOR DETECTING GLUCAGON-LIKE PEPTIDE-1 ANTAGONISTS AND AGONISTS

CROSS REFERENCE TO RELATED APPLICATION

This application is a continuation-in-part of U.S. Ser. No. 08/142,439 filed Nov. 24, 1993, now U.S. Pat. No. 5,670, 360 which is a national application of PCT/EP93/00697 filed Mar. 23, 1993, and claims priority under 35 U.S.C. 119 of Danish Application serial no. 398/92 filed Mar. 25, 1992, the contents of which are fully incorporated herein by reference.

FIELD OF THE INVENTION

The present invention relates to a recombinant glucagon-like peptide-1 (GLP-1) receptor, to a DNA construct which comprises a DNA sequence encoding a GLP-1 receptor, to methods of screening for antagonists of GLP-1 activity and to methods for functional screening for agonists of GLP-1 activity.

BACKGROUND OF THE INVENTION

As used in the present specification the designation GLP-1 comprises GLP-1(7-37) as well as GLP-1(7-36) amide.

Glucose-induced insulin secretion is modulated by a number of hormones and neurotransmitters. In particular, two gut hormones, glucagon-like peptide-1 (GLP-1) and gastric inhibitory peptide (GIP) potentiate the effect of glucose on insulin secretion and are thus called gluco-incretins (Dupre, in The Endocrine Pancreas, E. Samois Ed. (Raven Press, New York, (1991), 253–281) and Ebert and Creutzfeld, (Diabetes Metab. Rev. 3, (1987)). Glucagon-like peptide-1 is a gluco-incretin both in rat and in man (Dupre and Ebert and Creutzfeld, vide supra, and Kreymann et al. (Lancet 2 (1987), 1300)). It is part of the preproglucagon molecule (Bell et al. Nature 304 (1983), 368) which is proteolytically processed in intestinal L cells to GLP-1(1-37) and GLP-1(7-36)amide or GLP-1(7-37) (Mojsov et al. (J.Biol.Chem. 261 (1986), 11880) and Habener et al.: The Endocrine Pancreas E. Samois Ed. (Raven Press, New York (1991), 53–71). Only the truncated forms of GLP-1 are biologically active and both have identical effects on insulin secretion in beta cells (Mojsov et al. J.Clin.Invest 79 (1987), 616) and Weir et al. (Diabetes 38 (1989), 338). They are the most potent gluco-incretins so far described and are active at concentrations as low as one to ten picomolar. The stimulatory effect of these gluco-incretin hormones requires the presence of glucose at or above the normal physiological concentration of about 5 mM and is mediated by activation of adenylate cyclase and a rise in the intracellular concentration of cyclic AMP (Drucker et al. Proc.Natl.Acad.Sci. USA 84 (1987), 3434) and G'ke et al. (Am.J.Physiol. 257 (1989), G397). GLP-1 has also a stimulatory effect on insulin gene transcription (Drucker et al. Proc.Natl.Acad-.Sci. USA 84 (1987), 3434). In a rat model of non-insulin-dependent diabetes mellitus (NIDDM) is associated with a reduced stimulatory effect of GLP-1 on glucose-induced insulin secretion (Suzuki et al. Diabetes 39 (1990), 1320). In man, in one study, GLP-1 levels were elevated in NIDDM patients both in the basal state and after glucose ingestion; however, following a glucose load there was only a very small rise in plasma insulin concentration (qrskov et al. J.Clin.Invest. 87 (1991), 415). A recent study (Nathan et al. Diabetes Care 15 (1992), 270) showed that GLP-1 infusion could ameliorate postprandial insulin secretion and glucose disposal in NIDDM patients. Thus, as a further step in understanding the complex modulation of insulin secretion by gut hormones and its dysfunction in diabetes, we isolated and characterized a complementary DNA for the beta cell GLP-1 receptor and showed that it is part of a new family of G-coupled receptors.

DESCRIPTION OF THE INVENTION

The present invention relates to a recombinant glucagon-like peptide-1 (GLP-1) receptor.

More preferably, the invention relates to a GLP-1 receptor which comprises the amino acid sequence shown in SEQ ID No. 1, or an analogue thereof binding GLP-1 with an affinity constant, $K_D$, below 100 nM, preferably below 10 nM. In the present context, the term "analogue" is intended to indicate a naturally occurring variant (including one expressed in other animal species, in particular human) of the receptor or a "derivative" i.e. a polypeptide which is derived from the native GLP-1 receptor by suitably modifying the DNA sequence coding for the variant, resulting in the addition of one or more amino acids at either or both the C- and N-terminal ends of the native amino acid sequence, substitution of one or more amino acids at one or more sites in the native amino acid sequence, deletion of one or more amino acids at either or both ends of the native sequence or at one or more sites within the native sequence, or insertion of one or more amino acids in the native sequence.

In another aspect, the present invention relates to a DNA construct which comprises a DNA sequence encoding the GLP-1 receptor of the invention, as well as a recombinant expression vector carrying the DNA construct and a cell containing said recombinant expression vector.

In one embodiment of the invention, the GLP-1 receptor molecule may be provided in solubilised and/or reconstituted form.

In the present context "solubilised" is intended to indicate a receptor as present in detergent-solubilised membrane preparations. "Reconstituted" is intended to indicate a receptor solubilised in the prescience of essential cofactors, e.g. G-protein. In this embodiment the receptor may be in a reconstituted micellar form.

The DNA construct of the invention encoding the GLP-1 receptor preferably comprises the DNA sequence shown in SEQ ID No. 1, or at least a DNA sequence coding for a functional analogue thereof binding GLP-1 with an affinity below 100 nM, preferably below 10 nM or a suitable modification thereof. Examples of suitable modifications of the DNA sequence are nucleotide substitutions which do not give rise to another amino acid sequence of the GLP-1 receptor, but which may correspond to the codon usage of the host organism into which the DNA construct is introduced or nucleotide substitutions which do give rise to a different amino acid sequence and therefore, possibly, a different protein structure without, however, impairing the properties of the native variant. Other examples of possible modifications are insertion of one or several nucleotides into the sequence, addition of one or several nucleotides at either end of the sequence, or deletion of one or several nucleotides at either end or within the sequence.

Another example of a DNA construct of the invention is one which encodes a GLP-1 receptor variant particularly suitable for solubilisation and reconstitution.

The DNA construct of the invention encoding the present GLP-1 receptor may be prepared synthetically by established standard methods, e.g. the phosphoamidite method described by Beaucage and Caruthers, Tetrahedron Letters 22 (1981), 1859–1869, or the method described by Matthes et al., EMBO Journal 3 (1984), 801–805. According to the phosphoamidite method, oligonucleotides are synthesized, e.g. in an automatic DNA synthesizer, purified, annealed, ligated and cloned in suitable vectors.

The DNA construct of the invention may also be of genomic or cDNA origin, for instance obtained by preparing a genomic or cDNA library and screening for DNA sequences coding for all or part of the GLP-1 receptor of the invention by hybridization using synthetic oligonucleotide probes in accordance with standard techniques (cf. Sambrook et al., Molecular Cloning: A Laboratory Manual, 2nd Ed., Cold Spring Harbor, 1989). In this case, a genomic or cDNA sequence encoding the GLP-1 receptor may be modified at a site corresponding to the site(s) at which it is desired to introduce amino acid substitutions, e.g. by site-directed mutagenesis using synthetic oligonucleotides encoding the desired amino acid sequence for homologous recombination in accordance with well-known procedures.

Finally, the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques. The DNA construct may also be prepared by polymerase chain reaction using specific primers, for instance as described in U.S. Pat. No. 4,683,202 or Saiki et al., Science 239 (1988), 487–491.

The recombinant expression vector into which the DNA construct of the invention is inserted may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the GLP-1 receptor of the invention should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA encoding the GLP-1 receptor of the invention in mammalian cells are the SV40 promoter (Subramani et al., Mol. Cell Biol. 1 (1981), 854–864), the MT-1 (metallothionein gene) promoter (Palmiter et al., Science 222 (1983), 809–814) or the adenovirus 2 major late promoter. A suitable promoter for use in insect cells is the polyhedrin promoter (Vasuvedan et al., FEBS Lett. 311, (1992) 7–11). Suitable promoters for use in yeast host cells include promoters from yeast glycolytic genes (Hitzeman et al., J. Biol. Chem. 255 (1980), 12073–12080; Alber and Kawasaki, J. Mol. Appl. Gen. 1 (1982), 419–434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304 (1983), 652–654) promoters. Suitable promoters for use in filamentous fungus host cells are, for instance, the ADH3 promoter (McKnight et al., The EMBO J. 4 (1985), 2093–2099) or the tpiA promoter.

The DNA sequence encoding the GLP-1 receptor of the invention may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) terminators. The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The recombinant expression vector of the invention may further comprise a DNA sequence enabling the vector to replicate in the host cell in question. An example of such a sequence (when the host cell is a mammalian cell) is the SV40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate.

The procedures used to ligate the DNA sequences coding for the GLP-1 receptor of the invention, the promoter and the terminator, respectively, and to insert them into suitable vectors containing the information necessary for replication, are well known to persons skilled in the art (cf., for instance, Sambrook et al., op.cit.).

The host cell into which the expression vector of the invention is introduced may be any cell which is capable of producing the GLP-1 receptor of the invention and is preferably a eukaryotic cell, such as invertebrate (insect) cells or vertebrate cells, e.s. *Xenopus laevis* oocytes or mammalian cells, in particular insect and mammalian cells. Examples of suitable mammalian cell lines are the COS (ATCC CRL 1650), BHK (ATCC CRL 1632, ATCC CCL 10), CHL (ATCC CCL39) or CHO (ATCC CCL 61) cell lines. Methods of transfecting mammalian cells and expressing DNA sequences introduced in the cells are described in e.g. Kaufman and Sharp, J. Mol. Biol. 159 (1982), 601–621; Southern and Berg, J. Mol. Appl. Genet. 1 (1982), 327–341; Loyter et al., Proc.Natl.Acad.Sci. USA 79 (1982), 422–426; Wigler et al., Cell 14 (1978), 725; Corsaro and Pearson, Somatic Cell Genetics 7 (1981), 603, Graham and van der Eb, Virology 52 (1973), 456; and Neumann et al., EMBO J. 1 (1982), 841–845.

Alternatively, fungal cells (including yeast cells) may be used as host cells of the invention. Examples of suitable yeasts cells include cells of *Saccharomyces spp.* or *Schizosaccharomyces spp.*, in particular strains of *Saccharomyces cerevisiae*. Examples of other fungal cells are cells of filamentous fungi, e.g. *Aspergillus spp.* or *Neurospora spp.*, in particular strains of *Aspergillus oryzae* or *Aspergillus niger*. The use of *Aspergillus spp.* for the expression of proteins is described in, e.g., EP 272 277.

The GLP-1 receptor according to the invention may be produced by a method which comprises culturing a cell as described above in a suitable nutrient medium under conditions which are conducive to the expression of the GLP-1 receptor, and recovering the GLP-1 receptor from the culture. The medium used to culture the cells may be any conventional medium suitable for growing mammalian cells, such as a serum-containing or serum-free medium containing appropriate supplements. Suitable media are available from commercial suppliers or may be prepared according to published recipes (e.g. in catalogues of the American Type Culture Collection).

If the GLP-1 receptor has retained the transmembrane and (possibly) the cytoplasmic region of the native variant, it will be anchored in the membrane of the host cell, and the cells carrying the GLP-1 receptor may be used as such in the screening or diagnostic assay. Alternatively, the receptor may be a component of membrane preparations, e.g. in solubilised and/or reconstituted form as defined above.

The present invention also provides methods for detecting GLP-1 antagonists/inverse agonists. Within the context of the invention, an GLP-1 antagonist/inverse agonist is understood to refer to a molecule that reduces the GLP-1 stimulated response within a given cell.

Within one aspect of the present invention, methods are provided for detecting the presence of GLP-1 antagonists comprising the steps of (a) exposing the compound in the presence of a GLP-1 agonist to a recombinant GLP-1 receptor coupled to a response pathway under conditions and for a time sufficient to allow binding of the compound to the receptor and an associated response through the pathway, and (b) detecting a reduction in the stimulation of the response pathway resulting from the binding of the compound to the GLP-1 receptor, relative to the stimulation of the response pathway by the GLP-1 agonist alone and therefrom determining the presence of a GLP-1 antagonist/inverse agonist. Within the context of the present invention, GLP-1 agonists include molecules (including GLP-1 itself) capable of binding to a GLP-1 receptor, and which stimulate a response pathway within a cell.

A variety of compounds may be screened utilizing such methods. Representative examples include blocking antibodies, GLP-1 peptides and GLP-1 analogs (including both peptides and non-peptides).

The compounds are exposed to a recombinant GLP-1 receptor in the presence of a GLP-1 agonist under conditions and for a time sufficient to allow binding of the compound to the receptor, and an associated response though the pathway. As utilized in the present invention, conditions and times sufficient for the binding of the antagonist/inverse agonist to the receptor will vary with the source of the receptor, however, conditions suitable for the binding generally occur between 4° and 40° C. in a buffer solution and within a pH range of 5 and 9, preferable between 6.8 and 8. Sufficient time for the binding and response will generally be between 5 and 200 minutes after exposure.

Once the compound has been exposed to a recombinant GLP-1 receptor in the presence of a GLP-1 agonist, under conditions and for a time sufficient to allow binding of the compound to the receptor, a reduction in the stimulation of the response pathway may be detected if the compounds competes with the GLP-1 agonist for the recombinant GLP-1 receptor. Within one embodiment of the invention, the response pathway is a membrane bound adenylate cyclase response pathway, and the step of detecting comprises measuring a reduction in cAMP production by the membrane bound adenylate cyclase response pathway, relative to the cAMP production in the presence of GLP-1 agonist alone. Adenylate cyclase activity assays may be carried out, for example, utilizing method(s) described by Knudsen et al. (Eur. J. Pharmacol., 318, 429–435(1996)). Alternatively, cAMP may be measured by any other assay. Generally, these assays are well known in the art.

In another embodiment of the invention, the present invention relates to a method for functional screening for the presence of GLP-1 agonists, the method comprising the steps of:

(a) exposing a compound to a recombinant GLP-1 receptor coupled to a response pathway under conditions and for a time sufficient to allow binding of the compound to the receptor and an associated response through the pathway; and (b) detecting stimulation of the response pathway relative to the non stimulated pathway.

With a preferred embodiment of the invention a DNA construct is provided comprising a cAMP response element such as proenkephalin cAMP response element, which is operately linked to a luciferase cDNA. The DNA construct comprising the luciferase cDNA is then stably transfected into a host cell. The host cell is then transfected with a second DNA construct containing a first DNA segment encoding the GLP-1 receptor operably linked to additional DNA segments necessary for the expression of the receptor. Upon binding of the GLP-1 receptor agonist, the elevated cAMP levels induce the expression of luciferase. The luciferase is exposed to luciferin, and the photons released during the oxidation of luciferin by the luciferase is measured.

The solid support employed in the screening methods of the invention preferably comprises a polymer. The support may in itself be composed of the polymer or may be composed of a matrix coated with the polymer. The matrix may be of any suitable material such as glass, paper or plastic. The polymer may be selected from the group consisting of a plastic (e.g. latex, a polystyrene, polyvinylchloride, polyurethane, polyacrylamide, polyvinylalcohol, nylon, polyvinylacetate, and any suitable copolymer thereof), cellulose (e.g. various types of paper, such as nitrocellulose paper and the like), a silicon polymer (e.g. siloxane), a polysaccharide (e.g. agarose or dextran), an ion exchange resin (e.g. conventional anion or cation exchange resins), a polypeptide such as polylysine, or a ceramic material such as glass (e.g. controlled pore glass).

The physical shape of the solid support is not critical, although some shapes may be more convenient than others for the present purpose. Thus, the solid support may be in the shape of a plate, e.g. a thin layer or microtiter plate, or a film, strip, membrane (e.g. a nylon membrane or a cellulose filter) or solid particles (e.g. latex beads or dextran or agarose beads). In a preferred embodiment, the solid support is in the form of wheat germ agglutinin-coated SPA beads (cf. U.S. Pat. No. 4,568,649).

BRIEF DESCRIPTION OF THE DRAWINGS

The present invention is further illustrated in the following examples with reference to the appended drawings in which FIG. 1A and FIG. 1B which is a continuation of FIG. 1A together show the amino acid sequence of the rat GLP-1 receptor (SEQ ID NO:1) in a comparison with the sequence of the rat secreting receptor (SECR) (SEQ ID NO:5), the opossium parathyroid hormone receptor (PTHR) (SEQ ID NO:6) and the porcine calcitonin receptor (CTR1) (SEQ ID NO:7). The GLP-1 receptor has three N glycosylation sites in the extracellular domain (arrows). Four cysteines are conserved at identical places in the four receptor (boxes). Note the otherwise very divergent sequences in this part of the molecules as well as in the COOH-terminal cytoplasmic tail. Sequence identities are denoted by stars and homologies by dots. The location of the putative transmembrane domains are indicated by horizontal bars above the sequences.

Figure 2:
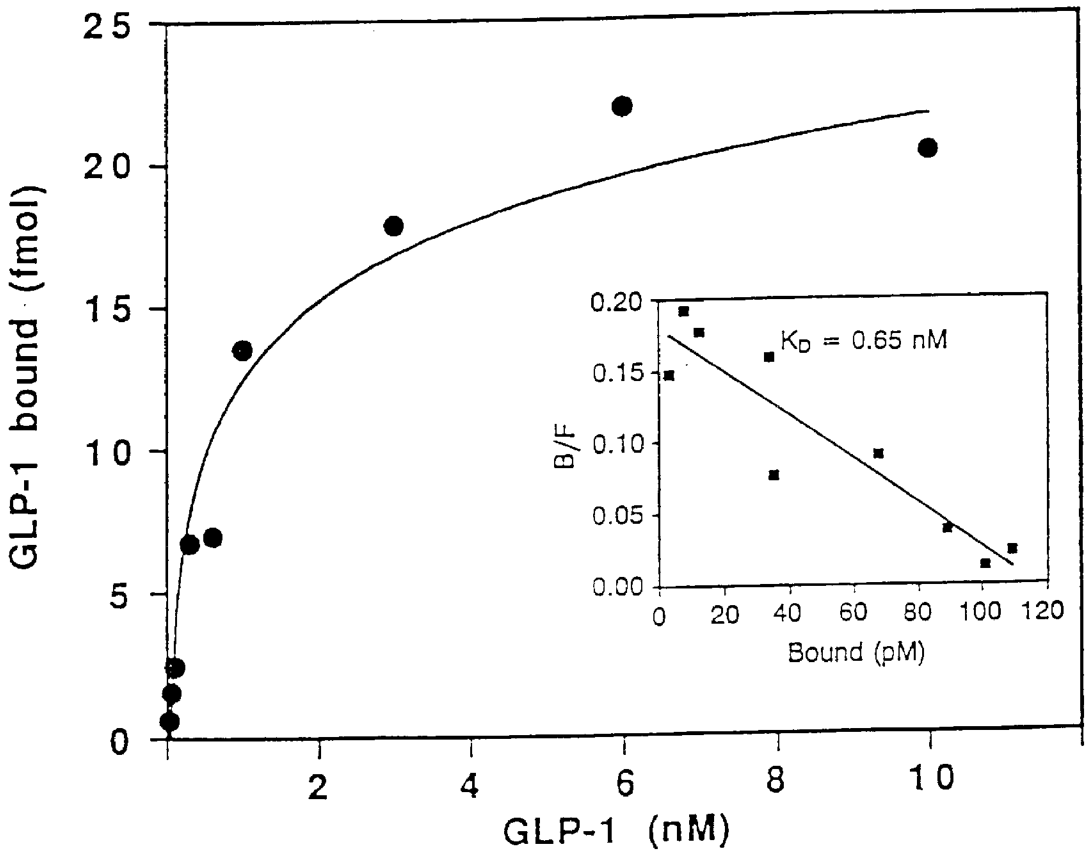
FIG. 2 shows binding of $^{125}$I-GLP-1 to COS cells transfected with the pGLPR-16 plasmid. Specific binding reaches saturation at 1 to 10 nM GLP-1. Insert: Scatchard analysis of GLP-1 binding.
Figure 3:
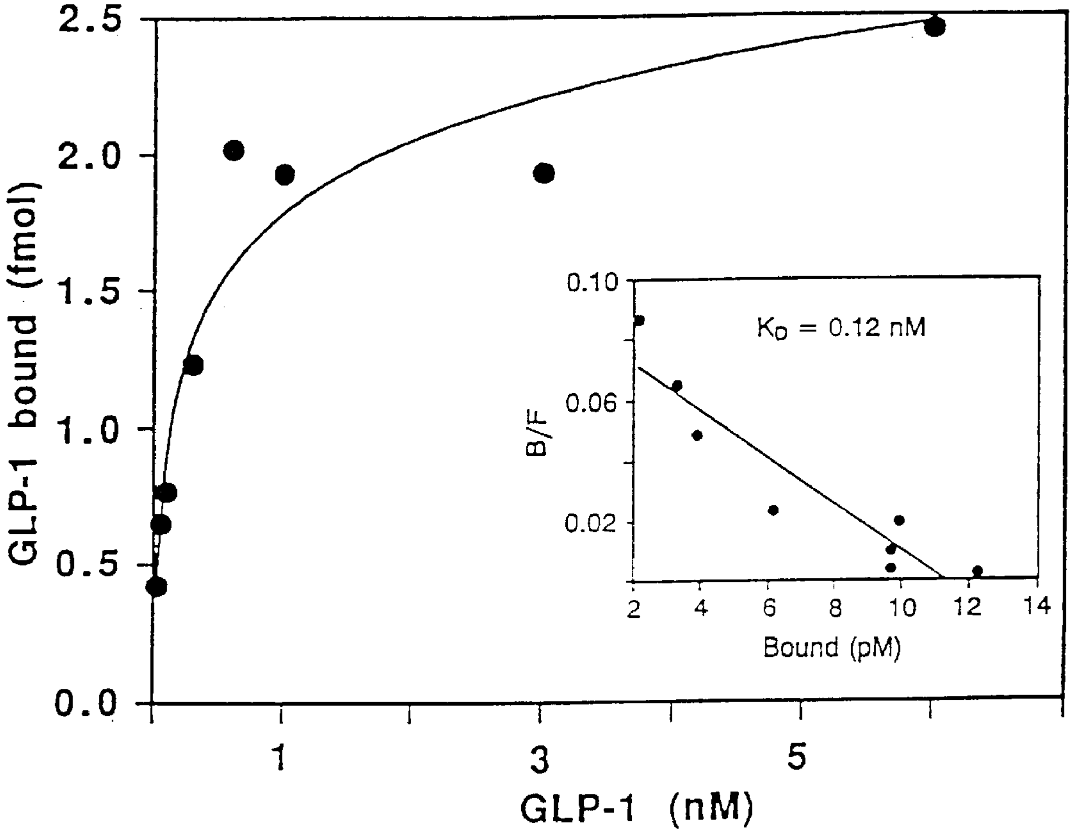
FIG. 3 shows binding of $^{125}$I-GLP-1 to INS-1 cells. Specific binding reaches saturation at 1 to 10 nM GLP-1. Insert: Scatchard analysis of GLP-1 binding.

Fitting of the curves in FIGS. 2 and 3 were performed with the LIGAND program (McPherson, Kinetic, EBDA, Ligand, Lowry. A Collection of radioligand analysis programs (Elsevier, Amsterdam, 1985)).

Figure 4:
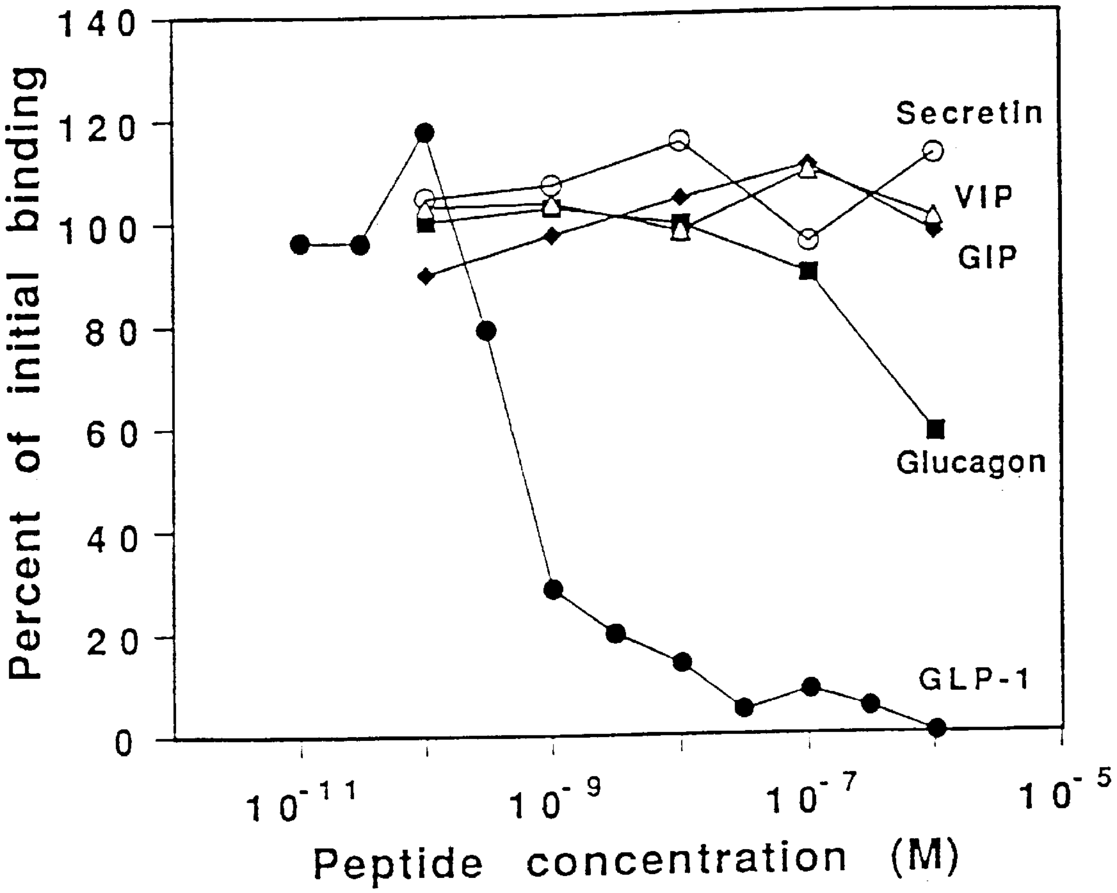

FIG. 4 shows displacement of $^{125}$I-GLP-1 binding to COS cells transfected with the rat GLP-1 receptor cDNA. Transfected cells were incubated with 20 pM $^{125}$I-GLP-1 in the presence of increasing concentrations of cold peptides. Each point was measured in duplicate and the experiments repeated three times for GLP-1, GIP and glucagon and once for VIP and secreting.

Figure 5:
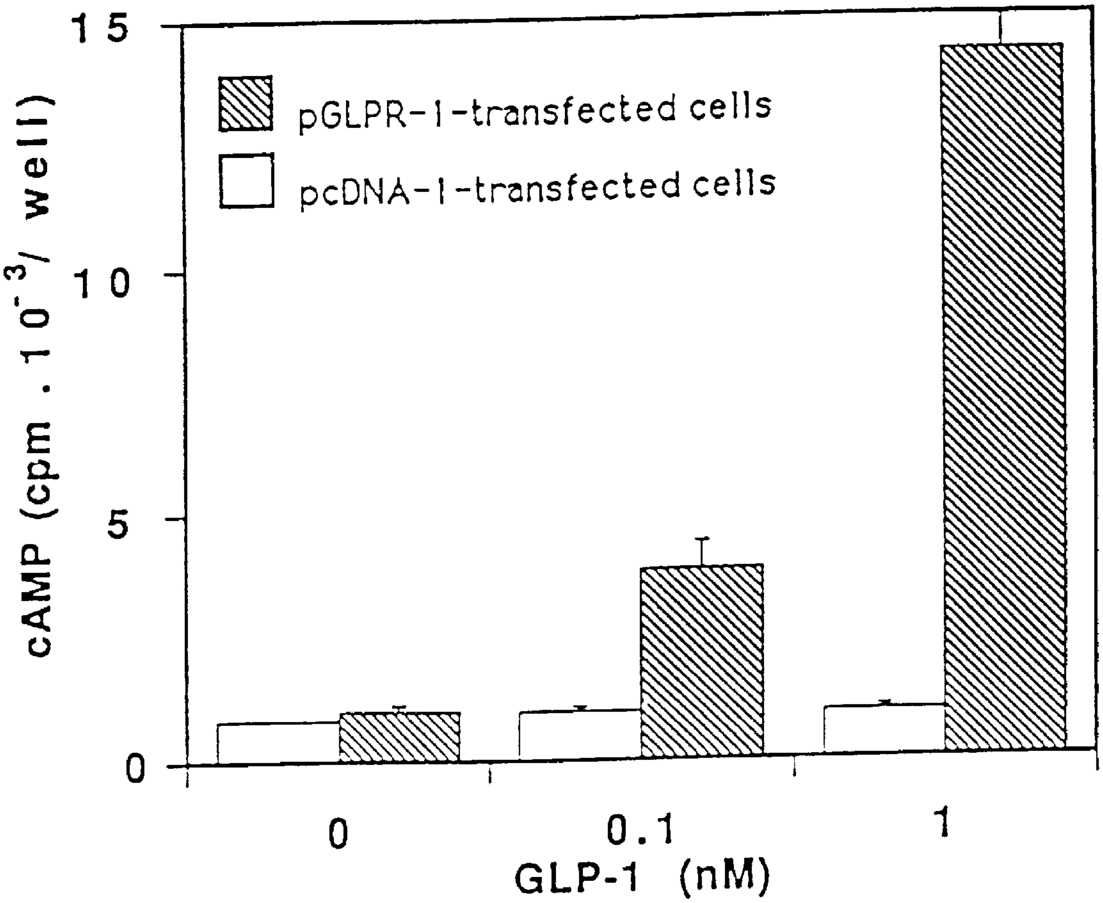

FIG. 5 shows stimulation of cyclic AMP formation in COS cells transfected with the rat GLP-1 receptor cDNA. COS cells were transfected with the pcDNA-1 vector alone (open bars) or the pGLPR-1 plasmid (stripped bar) and incubated in the absence or the presence of GLP-1 at the indicated concentration. cAMP production was measured in triplicate with a radioimmunoassay (Amersham).

Figure 6:
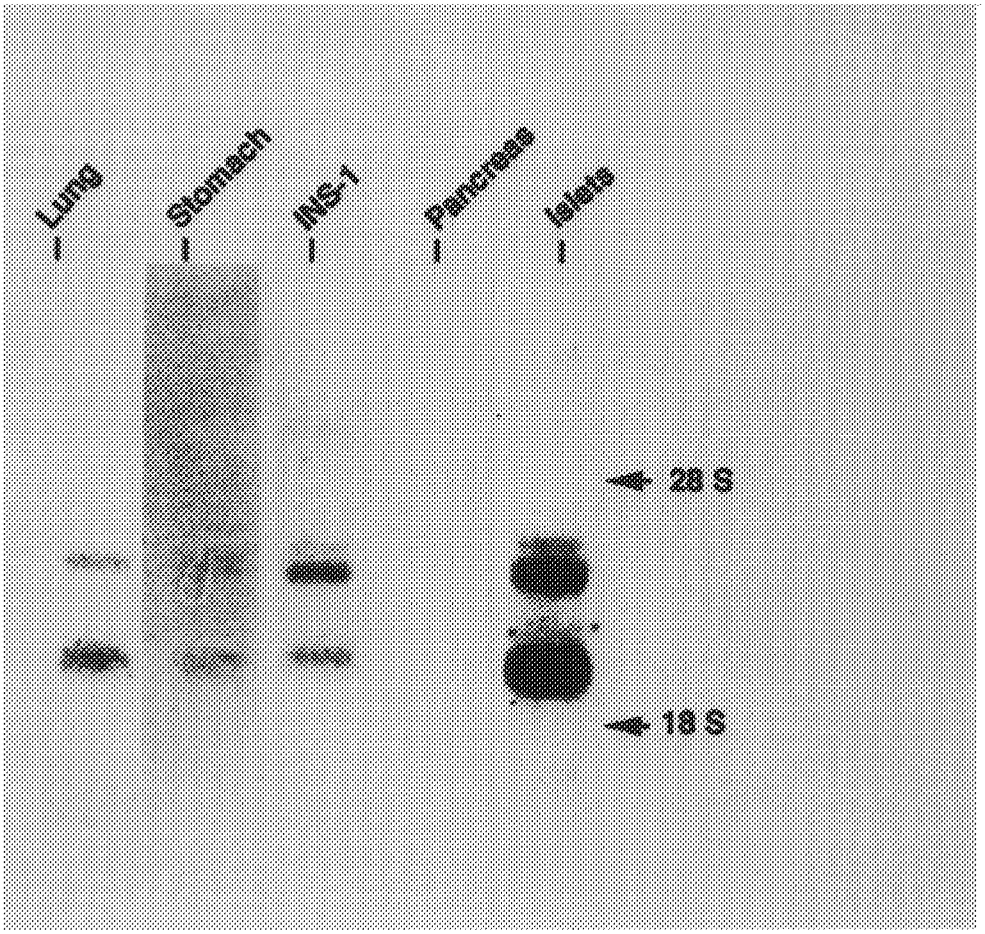

FIG. 6 shows tissue specificity of GLP-1 receptor expression assessed by Northern blotting of RNA from different tissues and from the INS-1 cell line. Ten micrograms of total RNA was analyzed on each lane. Two major RNA species of 2.7 and 3.6 kb were detected in all tissues in which the receptor was detected. The position of the migration of the ribosomal RNAs is indicated to the left of the picture.

FIG. 7 is a comparison of rat GLP-1 receptor (SEQ ID No.1) amino acid sequence (rat) and a partial amino acid sequence of the human GLP-1 receptor (SEQ ID No. 3) (human).

The present invention is further illustrated in the following examples which is not intended to be in any way limiting to the scope of the invention as claimed.

EXAMPLE 1

Molecular Cloning and Characterisation of the Rat Islet GLP-1 Receptor cDNA.

A rat pancreatic islet cDNA library was constructed in the pcDNA-1 expression vector (Rat pancreatic islets were prepared according to Gotoh et al. (Transplantation 43 (1985), 725). PolyA+ RNA was prepared and the cDNA library was constructed in the pcDNA-1 vector (In Vitrogen) as described by Aruffo and Seed (Proc.Natl.Acad.Sci. USA 84 (1987), 8573) and Lin et al. (Proc.Natl.Acad.Sci. USA 88 (1991), 3185). Plasmid DNA was prepared from pools of five to eight thousands bacterial clones (Maniatis et al., Molecular Cloning. A Laboratory Manual. Cold Spring Harbor Laboratory, 1982) and transfected into COS cells (Sompayrac and Dana, Proc.Natl.Acad.Sci. USA 78 (1981), 7575). The presence of GLP-1 receptor expressed in COS cells was assessed by binding of the radioiodinated peptide followed by photographic emulsion autoradiography and screening by dark field microscopy (Gearing et al. EMBO J. 8 (1989), 3667). GLP-1(7-36)amide, as well as the other peptides, were purchased from Peninsula Laboratories. Iodination was performed by the iodine monochloride method (Contreras et al. Meth.Enzymol. 92 (1983), 277), the peptide was purified by passage over Sephadex G-10 followed by CM-Sepharose and specific activity was determined by the self displacement technique (Calvo et al. Biochem. 212 (1983), 259). A 1.6 kb cDNA clone (pGLPR-1) was isolated by subfractionation of an original positive pool and was used to isolate, by DNA hybridization screening, two additional clones from primary positive pools. These plasmids (pGLPR-16 and -87) had inserts of 3.0 and 2.0 kb, respectively. Transfection of these clones into COS cells generated high affinity ($K_D$=0.6 nM) binding sites for GLP-1 (FIG. 2). This affinity is comparable to that seen for binding of GLP-1 to the rat insulinoma cell line INS-1 (Asfari et al. Endocrinology 130 (1992), 167) ($K_D$=0.12 nM; FIG. 3). In both cases a single high affinity binding component was detected. The binding to GLP-1 receptor transfected COS cells reached a plateau between 1 and 10 nM. At concentrations above 10 nM a second, high capacity, low affinity, binding component was detected. Although specifically displacable by cold GLP-1, this binding was also present in COS cells transfected with the expression vector alone and was therefore not further characterized.

Binding of GLP-1 to the receptor expressed in COS cells was displaced by cold GLP-1 with a 50 percent displacement achieved at 0.5 to 1 nM (FIG. 4). Other peptide hormones of related structure such as secreting, gastric inhibitory peptide (GIP) and vasoactive intestinal peptide (VIP) (Dupre in The Endocrine Pancreas, E. Samois Ed. (Raven Press, New York, (1991), 253–281) and Ebert and Creutzfeld, Diabetes Metab. Rev. 3, (1987) did not displace binding. Glucagon could displace the binding by 50 percent but only at a concentration of one micromolar (FIG. 4). The addition of subnanomolar concentrations of GLP-1 to transfected COS cells stimulated the production of cyclic AMP indicating that the receptor was functionally coupled to activation of adenylate cyclase (FIG. 5).

Figure 1A:
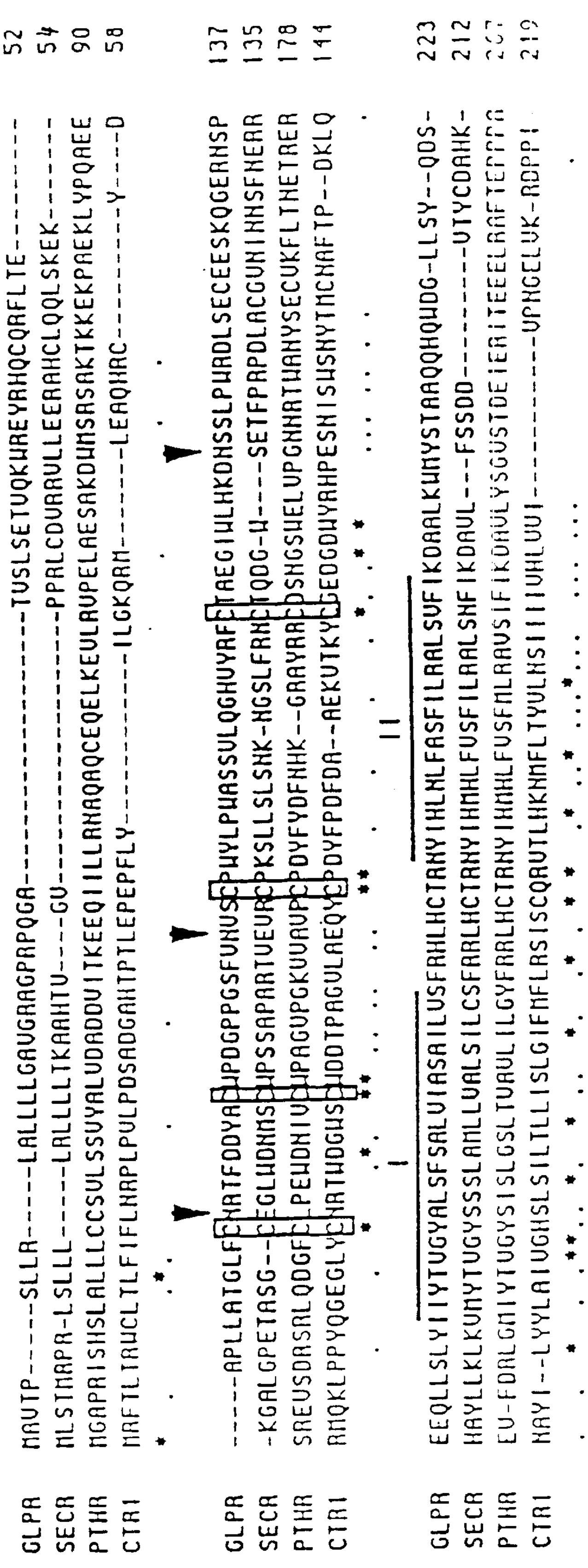

DNA sequence analysis of the rat GLP-1 receptor cDNA revealed a major open reading frame coding for a 463 amino acid polypeptide (SEQ ID No. 1). Hydrophaphy plot analysis indicated the presence of an amino-terminal hydrophobic region most probably representing a leader sequence. This hydrophobic segment is followed by a hydrophilic domain of about 120 amino acids which contains three N-linked glycosylation sites. Seven hydrophobic segments are present which may form transmembrane domains. Search for sequence identities showed the GLP-1 receptor to be homologous to the secreting receptor (Ishihara et al. EMBO J. 10 (1991), 1635) (40 percent identity), the parathyroid hormone receptor (Jhppner et al. (Science 254 (1991), 1024) (32.4 percent identity) and the calcitonin receptor (Lin et al. Science 254 (1991), 1022) (27.5 percent identity) (FIG. 1). These four receptors do not share any significant sequence homology with other known members of the G-coupled receptor family and are characterized by a relatively long amino terminal, probably extracellular, domain. The sequence of the extracellular domain is unique for each receptor, yet four cysteines are perfectly conserved (boxes in FIG. 1). A fifth cysteine at position 126 of the GLP-1 receptor is also conserved in the parathyroid and calcitonin receptors and at a similar location in the secreting receptor (position 123). The highest sequence identity between the four proteins resides in the transmembrane domains. The carboxyl terminal, cytoplasmic, ends of each receptor are also very different. These receptors all stimulate the production of cyclic AMP in response to ligand binding (Ishihara et al. EMBO J. 10 (1991), 1635), Jhppner et al. (Science 254 (1991), 1024) and Lin et al. Science 254 (1991), 1022) and are presumably coupled to the cyclase via Gs". In that respect, it is interesting to note that a sequence motif present in the third cytoplasmic loop of the GLP-1 receptors (RLAK, present just before the sixth transmembrane domain) is very similar to a motif of the beta2 adrenergic receptor (KALK) present at the same location and whose basic amino acids have been shown to be important in the coupling of the receptor to Gs" (Okamoto et al. Cell 67 (1991), 723). Moreover, in the beta2 adrenergic receptor, this motif is preceeded by a basic amino acid located twelve amino acid toward the amino-terminal end. This basic amino acid is also required at this particular distance for efficient coupling to Gs". In the GLP-1 receptor a lysine residue is also present at a similar location. This suggests that, despite the very low overall sequence identity, a structural feature may have been conserved in the third cytoplasmic loop between the two receptors which, may be required for the coupling of receptor to the Gs" protein.

Determination of the tissue distribution of the GLP-1 receptor was performed by Northern blot analysis. Northern blot analysis was performed with 10:g of total RNA (Chomczynski and Sacchi, Anal.Biochem. 126 (1987), 156) denatured with glyoxal (McMaster and Carmichael, Proc-.Natl.Acad.Sci. USA 74 (1977), 4835) separated on a 1% agarose gel and transferred to Nylon membranes (Thomas, Proc.Natl.Acad.Sci. USA 77 (1980), 5201). Hybridization was performed with the random primed labelled (Feinberg and Vogelstein, Anal.Biochem. 132 (1983), 6) 1,6 kb pGLPR-1 insert. Two mRNAs of 2.7 and 3.6 kb could be detected in pancreatic islets as well as in rat insulinoma cell lines (INS-1), in stomach and in lung (FIG. 6). No GLP-1 receptor mRNA could be detected in brain, liver, thymus, muscle, intestine and colon. The presence of the GLP-1 receptor has been reported in stomach where the peptide inhibits acid secretion by parietal cells in in vivo experiments (Schjoldager et al. Dig.Dis.Sci. 34 (1989), 703) but stimulates acid secretion on isolated parietal glands (Schmidtler et al. Am.J.Physiol. 260 (1991), G940). Binding sites for GLP-1 have also ben reported in lung membrane preparations (Richter et al. FEBS Letter 1 (1990), 78) but the role of the hormone on lung physiology is not known.

A stable cell line expressing the cloned rat GLP-1 receptor was established by Ca-phosphate mediated transfection (Maniatis et al., Molecular Cloning. A Laboratory Manual. Cold Spring Harbour Laboratory, 1989) of the CHL cell line (ATCC CCL39). The plasmid, pGLPR-1, which contains a 1.6 kb rat GLP-1 receptor cDNA insert cloned in the pcDNA-1 vector, was cotransfected with the pWL-neo plasmid (Stratagene, La Jolla, Calif.) into CHL cells. The pWL-neo plasmid contains the neomycin resistance gene. Stable clones were selected in medium containing 0.8 mg/ml G418. A stable transformant expressing an estimate of 70.000 rat GLP-1 receptors pr cell was selected by this scheme and further propagated in the presence of 80:M G418. Membranes from this transformant was subsequently used in the high-volume-throughput-screening (HVTS) assay as described in Example 3. Characterization of the receptor expressed by the GLP-1 R/CHL cell line led to an estimated Kd of 0.8 nM for whole cells, 2.3 nM for cell membranes using $^{125}$I-GLP-1(7-36)amide as radioligand.

EXAMPLE 2

Molecular cloning of the human islet GLP-1 receptor cDNA.

Human islets were prepared as described (Ricordi et al., Diabetes 37 (1988), 413–420), and poly-A$^+$ RNA was isolated by affinity chromatography by published methods (Gonda et al., Mol. Cell. Biol. 2 (1982) 617–624).

A human islet cDNA library was constructed in the 8ZAPII vector from Stratagene (La Jolla, Calif.). Briefly, double stranded cDNA was synthesized as previously described (Aruffo and Seed, 84 (1987), 8573–8577; Thorens, Proc.Natl.Acad.Sci., USA 89 (1992), 8641–8645), and EcoRI/NotI adaptors (Stratagene, La Jolla, Calif.) were added with $T_4$ DNA ligase.

The resulting cDNA molecules were phosphorylated with $T_4$ polynucleotide kinase before size fractionation on potassium acetate gradients (Aruffo and Seed, 84 (1987), 8573–8577).

Double stranded cDNA with a size above 1.6 kb was ligated into 8ZAPII arms (Stratagene, La Jolla, Calif.), packaged inr8 phage and grown on a lawn of XL-1 Blue *E. coli* cells as described in protocols from Stratagene.

The cDNA library was screened by hybridization to a $^{32}$P labelled DNA fragment from the rat GLP-1 receptor cDNA by previously described methods (Maniatis et al., Molecular Cloning. A Laboratory Manual. Cold Spring Harbour Laboratory, 1982).

The reduced stringency conditions used were: prehybridization and hybridization in 30% formamide, 5*SSC, 5*Denhardt, 50 mM phosphate buffer pH 6.8, 5 mM EDTA, 0.2% SDS and 100:g/ml salmon sperm DNA at 42EC. Washings were 4*30 min in 2*SSC, 0.2% SDS at 42EC (Maniatis et al., Molecular Cloning. A Laboratory Manual. Cold Spring Harbour Laboratory, 1982).

Positive 8 phages were purified by replating and hybridization, the cDNA inserts contained in the Bluescript vector present in the 8 ZAPII arms were excised using helper phages obtained from Stratagene (La Jolla, Calif.). The inserts were partially sequenced. One clone designated 3(20) showed high homology to the rat GLP-1 receptor and was sequenced (Tabor and Richardson, Proc.Natl.Acad.Sci., USA 84 (1987), 4767–4771) in its entire length. The DNA sequence is shown as SEQ ID No. 3.

From homology analysis (FIG. 7), it was concluded that this cDNA encoded the 3' part of the human GLP-1 receptor.

The deduced amino acid sequence of the human receptor has 92% identity to the rat GLP-1 receptor in the region from amino acid number 170 to amino acid number 463 (numbers refer to the rat sequence).

The isolated human GLP-1 cDNA does not contain the entire open reading frame at the 5' end. However, a full length clone can easily be obtained by methods well known to persons skilled in the art. Among the alternative methods of choice, the following examples should be mentioned: 1) The human islet cDNA library can either be rescreened with a probe from the 5' end of the already cloned sequence. 2) Anchor-PCR or RACE (Rapid Amplification of cDNA Ends) (Kriangkum et al., Nucleic Acids Res. 20 (1992) 3793–3794; Troutt et al., Proc.Natl.Acad.Sci., USA 89 (1992), 9823–9825) methodology can be used to clone the remaining 5' sequences from islet RNA. 3) The remaining 5' part can be isolated from human genomic libraries, and DNA fragments considered to represent introns can be identified based on homology to the cDNA of the rat receptor and deleted by mutagenesis.

After cloning of the 5' end of the open reading frame, this part of the cDNA can be fused to the remaining 3' part of the human GLP-1 receptor cDNA by the use of PCR or through fusion at appropriate restriction enzyme recognition sequences identified in both the 5' and the 3' parts.

The cDNA encoding the full length open reading frame can be cloned in suitable mammalian expression vectors and transfected into mammalian cell lines for expression. Examples of such suitable cell lines are the CHO and CHL cells, but other mammalian cells will also express receptors of this type.

It has recently been demonstrated that insect cells (Vasudevan et al. FEBS Lett. 311 (1992), 7–11) and micro-organisms like e.g. yeast (King et al., Science 250 (1990), 121–123) can express G-protein coupled receptors.

Recently frog skin melanophore cells have been used to express G-protein coupled receptors (Potenza et al, Analytical Biochem., 206, (1992), 315–322) and a functional coupling to adenylate cyclase was demonstrated.

Other microorganisms like Aspergillus, Bacillus, *E. coli* might be able to express these receptors after appropriate genetic engineering and selection.

It is therefore clear to persons skilled in the art that a number of different expression systems can be designed that will lead to expression of a functional receptor molecule.

As demonstrated in Example 3, the rat as well as the human GLP-1 receptor can be used in screening assays for detection of new potential agonist lead structures.

EXAMPLE 3

High throughput screening assay for GLP-1 receptor agonists.

Screening of microbial extracts for secondary metabolites with potential GLP-1 agonist activity was carried out using the SPA (Scintillation Proximity Assay) technology (U.S. Pat. No. 4,568,649, Hart and Greenwalt (Mol. Immunol., 16 (1979) 265–267), Udenfriend et al (Proc.Natl.Acad.Sci. USA, 82 (1985) 8672-8676). Wheatgerm agglutinin (WGA) coated SPA beads developed by Amersham International were used (U.S. Pat. No. 4,568,649, European patent 0154734, Japanese patent appl. 84/52452). The WGA coat allows GLP-1 receptor bearing membranes to be immobilized on the SPA beads. Membranes used in the screening assay were prepared from a CHL, (ATTC CCL39) cell line expressing the cloned rat GLP-1 receptor as described in in Example 1. Membranes were prepared essentially as decribed by Unden et al (Eur. J. Biochem. 145 (1984), 525–530). The binding of $^{125}$I-GLP-1(7-36)amide to such immobilized receptors brings the tracer in close proximity to the scintillant present within the SPA beads resulting in the emission of light. Any unbound ligand will not generate a signal. Thus under assay conditions a microbial extract—containing a component capable of binding to the GLP-1 receptor and thereby displacing the tracer—may be identified by virtue of a reduction in signal intensity.

A high throughput assay was established using 96 well microtiter plates. The assay was optimized with regard to the amounts of WGA particles, membrane and tracer used. (The 125I-GLP-1(7-36)amide tracer was labelled using the lactoperoxidase method (Morrison et al., Methods Enzymol. 70 (1980), 214–219) followed by purification on reverse phase HPLC). Using a Packard TopCount™ microplate scintillation counter (Packard Instrument Company) these optimized conditions resulted in a $B_0$ of more than 7000 cpm. (Non specific binding determined in the presence of 500 nM unlabelled GLP-1(7-36)amide amounts to less than 1000 cpm. $IC_{50}$=0.5–1.0 nM GLP-1(7-36) amide).

So far 1250 microbial extracts have been screened using the SPA GLP-1 receptor assay. The extracts were tested at a final dilution of 1:400. Under these conditions 15 out of the 1250 extracts resulted in a reduction of specific counts to below the chosen cut-off level. These 15 hits have been further characterized in a secondary assay. This secondary assay was designed to test whether cAMP synthesis in a GLP-1 receptor bearing cell line can be induced by components in the extract. $-TC3 cells (Hanahan et al., Nature 315 (1985) 115–122) and Efrat et al (Proc.Natl.Acad.Sci. USA 85 (1988) 9037–9041) grown in 96-well microtiter plates were exposed to extracts diluted in culture media. After 20 min at 37° C. the cells were lysed by addition of acid and the cAMP concentration determined using the cyclic AMP SPA system (Amersham International). Of the 15 primary hits tested in this secondary assay, 5 extracts have been found to significantly increase the cAMP level in $-TC3 cells.

It has thus been demonstrated that it is feasible that the screening approach described in this patent application can result in the isolation of natural compounds with GLP-1 agonist activity. The use of such compunds as lead structures for a medicinal chemistry approach will be of significant importance in the design of novel GLP-1 agonists.

EXAMPLE 4

Functional screening for GLP-1 antagonists.

Baby hamster kidney (BHK) cells expressing the human pancreatic GLP-1 receptor were used. Plasma membranes were prepared (Adelhorst et al, 1994, J. Biol. Chem. 269, 6275) by homogenization in buffer (10 mmol/l Tris-HCL and 30 mmol/l NaCL pH 7.4, containing, in addition, 1 mmol/l dithiothreitol, 5 mg/l leupeptin (Sigma, St. Louis, Mo., USA), 5 mg/l pepstatin (Sigma, St. Louis, Mo., USA), 100 mg/l bacitracin (Sigma, St. Louis, Mo., USA), and 16 mg/l aprotinin (Novo Nordisk A/S, Bagsvaerd, Denmark)). The homogenate was centrifuged on top of a layer of 41 w/v % sucrose. The white band between the two layers was diluted in buffer and centrifuged. Plasma membranes were stored at −80° C. until used.

The assay was carried out in 96-well microtiter plates in a total volume of 150 ml. The buffer used was 50 mmol/l Tris-HCl, pH 7.4 with the addition of 1 mmol/l EGTA, 1.5 mmol/l $MgSO_4$, 1.7 mmol/l ATP, 20 mM GTP, 2 mmol/l 3-isobutyl-1-methylxanthine (IBMX), 0.01% tween-20 and 0.1% human serum albumin (HSA) (Reinst, Behringwerke AG, Marburg, Germany). $10^{-9}$M GLP-1 and compounds to be screened for antagonist activity were diluted in buffer, added to the membrane preparation and the mixture was incubated for 2 h at 37° C. The reaction was stopped by the addition of 25 ml of 0.05 mol/l HCL. Samples were diluted 10 fold before analysis for cAMP by a scintillation proximity assay (RPA 538, Amersham, UK). The following results indicate no antagonists were identified

| | fmol cAMP (10) |
|---|---|
| $10^{-9}$M GLP-1 | 26.2 |
| 0 | 4.55 |
| $10^{-9}$M GLP-1 | 24.7 |
| 0 | 4.30 |
| $10^{-9}$M GLP-1 | 30.4 |
| 0 | 5.98 |
| $10^{-9}$M GLP-1 | 33.0 |
| 0 | 6.73 |
| $10^{-9}$M GLP-1 + S1 | 22.5 |
| $10^{-9}$M GLP-1 + S1 | 43.1 |
| $10^{-9}$M GLP-1 + S1 | 41.7 |
| $10^{-9}$M GLP-1 + S2 | 42.3 |
| $10^{-9}$M GLP-1 + S2 | 37.2 |
| $10^{-9}$M GLP-1 + S2 | 41.5 |
| $10^{-9}$M GLP-1 + S3 | 38.2 |
| $10^{-9}$M GLP-1 + S3 | 28.4 |
| $10^{-9}$M GLP-1 + S3 | 34.6 |

EXAMPLE 5

Functional screening for GLP-1 agonists.

The assay was carried out as in example 4 except compounds were added alone and not together with GLP-1. The following results indicate no agonists were identified.

-continued

| | fmol cAMP (10) |
|---|---|
| $10^{-13}$M GLP-1 | 5.00 |
| $10^{-12}$M GLP-1 | 6.14 |
| $10^{-11}$M GLP-1 | 5.03 |
| $10^{-10}$M GLP-1 | 23.9 |
| $10^{-9}$M GLP-1 | 42.9 |
| $10^{-8}$M GLP-1 | 46.8 |
| $10^{-7}$M GLP-1 | 57.3 |
| S1 | 9.86 |
| S2 | 6.72 |
| S3 | 7.87 |
| S4 | 8.52 |
| S5 | 7.88 |
| S6 | 8.48 |
| S7 | 8.16 |
| S8 | 5.89 |
| S9 | 4.35 |
| S10 | 5.64 |

What is claimed is:

1. A method for detecting the presence of a gucagon-like peptide-1 (GLP-1) antagonist, comprising the steps of:

(a) exposing a compound in the presence of GLP-1 agonist to a GLP-1 receptor produced in a heterologous exression system and coupled to a response pathway under conditions md for a time sufficient to allow binding of the compound to the receptor and an associated response through the pathway, wherein the GLP-1 receptor is a GLP-1 tecetor polypeptide having the amino acid sequence of a naturally occurring mammalian GLP-1 receptor encoded by cDNA molecule isolated from a mammalian library and comprisig a nucleotide sequence selected from the group consisting of (i) SEQ ID NO:1, (ii) SEQ ID NO:3, and (iii) the sequence of cDNA molecule capable of specifically hybridizing with a probe having the sequence of the complement of SEQ ID NO: 1 or SEQ ID NO: 3 under conditions of reduced stringency, wherein a probe having the sequence of the complement of SEQ ID NO: 1 will specifically identify a cDNA comprising the sequence shown in SEQ ID NO: 3 in a human cDNA library, said receptor polypeptide capable of binding GLP-1 with $K_D$ of less than 100 nM; and (b) detecting a reduction in the stimulation of the response pathway resulting from the binding of the compound to the GTP-1 receptor, relative to the stimulation of the response pathway by the GLP-1 agonist alone and therefrom determiring the presence of a GLP-1 antagonist.

2. The method of claim 1 wherein the response pathway is a membrane-bound adenylate cyclase response pathway.

3. The method of claim 2 wherein the step of detecting comprises measuring a reduction in cyclic AMP production by the membrane-bound adenylate cyclase response pathway.

4. The method of claim 1 wherein the response pathway includes a luciferase reporter system.

5. The method of claim 1, wherein the GLP-1 receptor polypeptide has the sequence of a GLP-1 receptor of rat or human origin.

6. The method of claim 1, wherein the expression system comprises heterologous DNA comprising the nucleotide sequence shown in SEQ ID NO: 1.

7. A method for detecting the presence of a GLP-1 agonist, comprising the steps of:

(a) exposing a compound to a GLP-1 receptor produced in a heterologous expression system and coupled to a response pathway under conditions and for a time sufficient to allow binding of the compound to the receptor and an associated response through the pathway, wherein the GLP-1 recptor is a GLP-1 receptor polypeptide having the amino acid sequence of a naturally occurring mammalian GLP-1 receptor encoded by cDNA molecule isolated from a mammalian library and comprising a nucleotide sequence selected from the group consisting of (i) SEQ ID NO:1, (ii) SEQ ID NO:3, and (iii) the sequence of cDNA molecule capable of specifically hybridizing with a probe having the sequence of the complement of SEQ NO: 1 or SEQ ID NO: 3 under conditions of reduced stringency, wherein a probe having the sequence of the complement of SEQ ID NO: 1 will specifically identify a cDNA comprising the sequence shown in SEQ ID NO: 3 in a human cDNA library, said receptor polypeptide capable of binding GLP-1 with $K_D$ of less than 100 nM; and (b) detecting stimulation of the response pathway relative to the non stimulated pathway.

8. The method of claim 7 wherein the response pathway is a membrane-bound adenylate cyclase response pathway.

9. The method of claim 8 wherein the step of detecting comprises measuring a production in cyclic AMP production by the membrane.

10. The method of claim 7 wherein the response pathway includes a luciferase reporter system.

11. The metlod of claim 7, wherein the GLP-1 receptor polypeptide has the sequence of a GLP-1 receptor of rat or human origin.

12. The method of claim 7, wherein the expression system comprises heterologous DNA comprising the nucleotide sequence shown in SEQ ID NO: 1.

* * * * *

UNITED STATES PATENT AND TRADEMARK OFFICE

CERTIFICATE OF CORRECTION

PATENT NO. : 5,846,747

DATED : December 8, 1998

INVENTOR(S) : Thorens et al.

It is certified that error appears in the above-indentified patent and that said Letters Patent is hereby corrected as shown below:

Col. 1, line 11, delete "Mar. 25, 1992" and insert --Mar. 25, 1993--.

Col. 2, line 39, delete "prescience" and insert --presence--.

Col. 9, line 38, delete "pcDNA" and insert --pCDNA-1"--.

Col. 10, line 7, delete "inr8" and insert --in 8--.

Col. 11, line 10, delete "lcad" and insert --lead--.

Col. 35, line 45, delete "md" and insert --and--.

Col. 35, line 48, delete "tecetor" and insert --receptor--.

Col. 35, line 51, delete "comprisig" and insert --comprising--.

Col. 36, line 60, delete "recptor" and insert --receptor--.

Signed and Sealed this

Nineteenth Day of October, 1999

Attest:

Q. TODD DICKINSON

*Attesting Officer* *Acting Commissioner of Patents and Trademarks*